US007591860B2

(12) United States Patent
Sabelle et al.

(10) Patent No.: US 7,591,860 B2
(45) Date of Patent: Sep. 22, 2009

(54) N-ALKYLPOLYHYDROXYLATED SECONDARY PARA-PHENYLENEDIAMINES, DYE COMPOSITIONS COMPRISING THEM, PROCESSES, AND USES THEREOF

(75) Inventors: Stéphane Sabelle, Paris (FR); Christian Blaise, Saint Mande (FR); Philippe Breton, Noisy le Roi (FR); Jean-Jacques Vandenbossche, Begaar (FR)

(73) Assignee: L'Oreal, S.A., Paris (FR)

( * ) Notice: Subject to any disclaimer, the term of this patent is extended or adjusted under 35 U.S.C. 154(b) by 206 days.

(21) Appl. No.: 11/066,462

(22) Filed: Feb. 28, 2005

(65) Prior Publication Data
US 2006/0026777 A1 Feb. 9, 2006

Related U.S. Application Data

(60) Provisional application No. 60/569,630, filed on May 11, 2004.

(30) Foreign Application Priority Data
Feb. 27, 2004 (FR) .................... 04 02020

(51) Int. Cl.
*A61K 8/00* (2006.01)
(52) U.S. Cl. ............... 8/405; 8/401; 8/406; 8/408; 8/421; 8/409
(58) Field of Classification Search ............. 424/401; 8/405
See application file for complete search history.

(56) References Cited

U.S. PATENT DOCUMENTS

| 2,436,115 | A | * | 2/1948 | Dickey et al. ............... 534/850 |
| 4,003,699 | A | | 1/1977 | Rose et al. |
| 4,823,985 | A | | 4/1989 | Grollier et al. |
| 4,979,961 | A | * | 12/1990 | Junino et al. .................... 8/410 |
| 5,032,137 | A | * | 7/1991 | Junino et al. .................... 8/410 |
| 5,041,143 | A | * | 8/1991 | Lang et al. ..................... 8/415 |
| 5,053,052 | A | * | 10/1991 | Junino et al. .................... 8/412 |
| 5,061,289 | A | | 10/1991 | Clausen et al. |
| 5,084,067 | A | * | 1/1992 | Junino et al. .................... 8/421 |
| 5,114,429 | A | * | 5/1992 | Junino et al. .................... 8/410 |
| 5,145,483 | A | * | 9/1992 | Junino et al. .................... 8/412 |
| 5,380,340 | A | | 1/1995 | Neunhoeffer et al. |
| 5,534,267 | A | | 7/1996 | Neunhoeffer et al. |
| 5,663,366 | A | | 9/1997 | Neunhoeffer et al. |
| 5,708,151 | A | | 1/1998 | Möckli |
| 5,766,576 | A | | 6/1998 | Löwe et al. |
| 6,099,592 | A | | 8/2000 | Vidal et al. |
| 6,284,003 | B1 | | 9/2001 | Rose et al. |
| 6,338,741 | B1 | | 1/2002 | Vidal et al. |
| 6,383,231 | B1 | * | 5/2002 | Lang et al. ..................... 8/405 |
| 6,471,730 | B1 | * | 10/2002 | Lang et al. ..................... 8/405 |
| 6,537,328 | B1 | * | 3/2003 | Lang et al. ..................... 8/405 |
| 6,890,362 | B2 | * | 5/2005 | Lang ............................. 8/405 |

| 2002/0050013 | A1 | 5/2002 | Vidal et al. |
| 2003/0019051 | A9 | 1/2003 | Vidal et al. |
| 2003/0167579 | A1 | 9/2003 | Lang |

FOREIGN PATENT DOCUMENTS

| DE | 23 59 399 | 6/1975 |
| DE | 38 43 892 A1 | 6/1990 |
| DE | 41 33 957 A1 | 4/1993 |
| DE | 195 43 988 A1 | 5/1997 |
| EP | 0 299 497 A | 1/1989 |
| EP | 0 714 954 B1 | 6/1996 |
| EP | 0 770 375 B1 | 5/1997 |
| FR | 2 586 913 A1 | 3/1987 |
| FR | 2 733 749 A1 | 11/1996 |
| GB | 1 026 978 | 4/1966 |
| GB | 1 153 196 | 5/1969 |
| JP | 2-19576 | 1/1990 |
| JP | 5-163124 | 6/1993 |
| JP | 09328129 | * 11/1997 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 01/66070 A | 9/2001 |

OTHER PUBLICATIONS

Hiyoshizo Kotsukl et al., "High Pressure Organic Chemistry; XII. A Convenient Synthesis of Aromatic Amines from Activated Aromatic Fluorides," Synthesis, Journal of Synthetic Organic Chemistry, vol. 12, pp. 1147-1148 (1999).
S. Massa et al., "Spiro-[4H-pyrrolo[1,2-a][1,4]benzodiazepine-4,4'-piperidine] Derivatives as Potential Nootropic Agents: A Simple One-Pot Synthesis," Synthetic Communications, vol. 20, No. 22, pp. 3537-3545 (1990).
English language abstract of EP 0 770 375 B1, May 2, 1997.
English language abstract of JP 2-19576, Jan. 23, 1990.
English language abstract of JP 5-163124, Jun. 29, 1993.

* cited by examiner

*Primary Examiner*—Johann R Richter
*Assistant Examiner*—Danielle Sullivan
(74) *Attorney, Agent, or Firm*—Finnegan, Henderson, Farabow, Garrett & Dunner, LLP

(57) ABSTRACT

The present disclosure relates to novel N-alkylpolyhydroxylated secondary para-phenylenediamines, to processes for preparing them, to compositions for dyeing keratin fibers, for example keratin fibers such as the hair, comprising, in a medium that is suitable for dyeing, at least one such secondary para-phenylenediamine. The present disclosure also relates to processes for dyeing keratin fibers with the compositions according to the present disclosure, and to dyeing kits containing such compositions.

18 Claims, No Drawings

N-ALKYLPOLYHYDROXYLATED SECONDARY PARA-PHENYLENEDIAMINES, DYE COMPOSITIONS COMPRISING THEM, PROCESSES, AND USES THEREOF

This application claims benefit of U.S. Provisional Application No. 60/569,630, filed May 11, 2004, and French Application No. 0402020, filed Feb. 27, 2004, which are herein incorporated by reference.

The present disclosure relates to a novel family of N-alkylpolyhydroxylated secondary para-phenylenediamines, to their preparation, to cosmetic compositions comprising them, and to processes of dyeing keratin fibers, such as hair, using these compositions.

It is known practice to dye keratin fibers, for instance keratin fibers such as hair, with dye compositions comprising oxidation dye precursors, such as ortho- or para-phenylenediamines, ortho- or para-aminophenols, and heterocyclic compounds, which are generally referred to as oxidation bases. Oxidation bases are colorless or weakly colored compounds which, when combined with oxidizing products, may give rise to colored compounds by a process of oxidative condensation.

It is also known that the shades obtained with oxidation bases may be varied by combining them with couplers or coloration modifiers. The coloration modifiers can be chosen, for example, from aromatic meta-diaminobenzenes, meta-aminophenols, meta-diphenols, and certain heterocyclic compounds such as indole compounds.

The variety of molecules used as oxidation bases and couplers makes it possible to obtain a wide range of colors.

The "permanent" coloration obtained using oxidation dyes must moreover satisfy a certain number of requirements. First, it should have no toxicological drawbacks. Second, it should allow shades of the desired intensity to be obtained. Third, it should have good resistance to external agents such as light, bad weather, washing, permanent waving, perspiration, and rubbing.

The dyes should also allow white keratin fibers to be covered. They should also be as unselective as possible, that is to say that they should allow the smallest possible differences in coloration to be produced over the entire length of the same keratin fiber, which is generally differently sensitized (that is to say damaged) between its end and its root.

The Inventor has discovered, surprisingly and unexpectedly, that it is possible to obtain a novel family of N-alkylpolyhydrodxylated secondary para-phenylenediamines capable of giving strong, aesthetic, and sparingly selective colorations in varied shades, and capable of showing good resistance to the various attacking factors to which keratin fibers may be subjected. Accordingly, the present disclosure relates to processes for preparing these N-alkylpolyhydroxylated secondary para-phenylenediamines and to their use in the oxidation dyeing of keratin fibers, such as hair.

Another aspect of the present disclosure relates to compositions for dyeing keratin fibers, for example human keratin fibers such as hair, comprising at least one secondary para-phenylenediamine bearing a polyhydroxylated group. Thesedye compositions can have the above mentioned advantages. In addition, these compositions can have a good toxicological profile.

Still another aspect of the present disclosure relates to dyeing processes using these compositions, comprising applying the compositions according to the present disclosure to keratin fibers, for example human keratin fibers such as hair. Another aspect of the present disclosure relates to multi-compartment devices or dyeing kits comprising the compositions described herein.

The compositions of the present disclosure make it possible to obtain very powerful, sparingly selective, and fast, for example light-fast, dyeing of keratin fibers, while at the same time avoiding the degradation of these fibers.

Other characteristics, aspects, and benefits of the present disclosure will emerge even more clearly upon reading the description and the examples that follow.

The novel secondary para-phenylenediamines according to the present disclosure are chosen from compounds of formula (I), and the addition salts thereof:

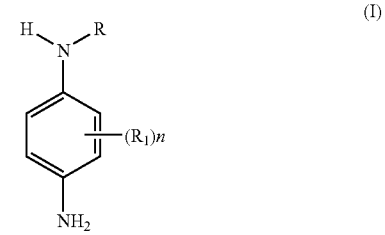

wherein:
R is chosen from linear and branched $C_2$-$C_{18}$ alkyl radicals comprising from 2 to 4 hydroxyl groups, wherein the alkyl radicals are unsubstituted or substituted with at least one entity chosen from amino, mono($C_1$-$C_{15}$)alkylamino, di($C_1$-$C_{15}$)alkylamino, ($C_1$-$C_{15}$)alkylcarbonyl, amido, mono($C_1$-$C_{15}$)alkylaminocarbonyl, and di($C_1$-$C_{15}$)alkylaminocarbonyl groups, and wherein the alkyl radicals are optionally interrupted with at least one heteroatom chosen from oxygen and nitrogen;
$R_1$ is chosen from hydrogen atoms, $C_1$-$C_{15}$ alkyl radicals, $C_1$-$C_{15}$ alkoxy radicals, hydroxy(($C_1$-$C_{15}$)alkoxy) radicals, ($C_1$-$C_{15}$)alkoxy($C_1$-$C_{15}$)alkyl radicals, $C_1$-$C_{15}$ monohydroxyalkyl radicals, $C_1$-$C_{15}$ polyhydroxyalkyl radicals, and halogen atoms;
n is an integer ranging from 1 to 4;

wherein the compound is not N-(2,3-dihydroxypropyl)-para-phenylenediamine.

In one embodiment, the group R of formula (I) is chosen from linear and branched $C_2$-$C_{18}$ alkyl radicals comprising from 2 to 4 hydroxyl groups, wherein the alkyl radical may be optionally interrupted with at least one heteroatom chosen from oxygen and nitrogen; and the group $R_1$ of formula (I) is chosen from hydrogen, $C_1$-$C_6$ alkyl radicals, and $C_1$-$C_6$ alkoxy radicals.

The compounds of general formula (I) may be chosen from:
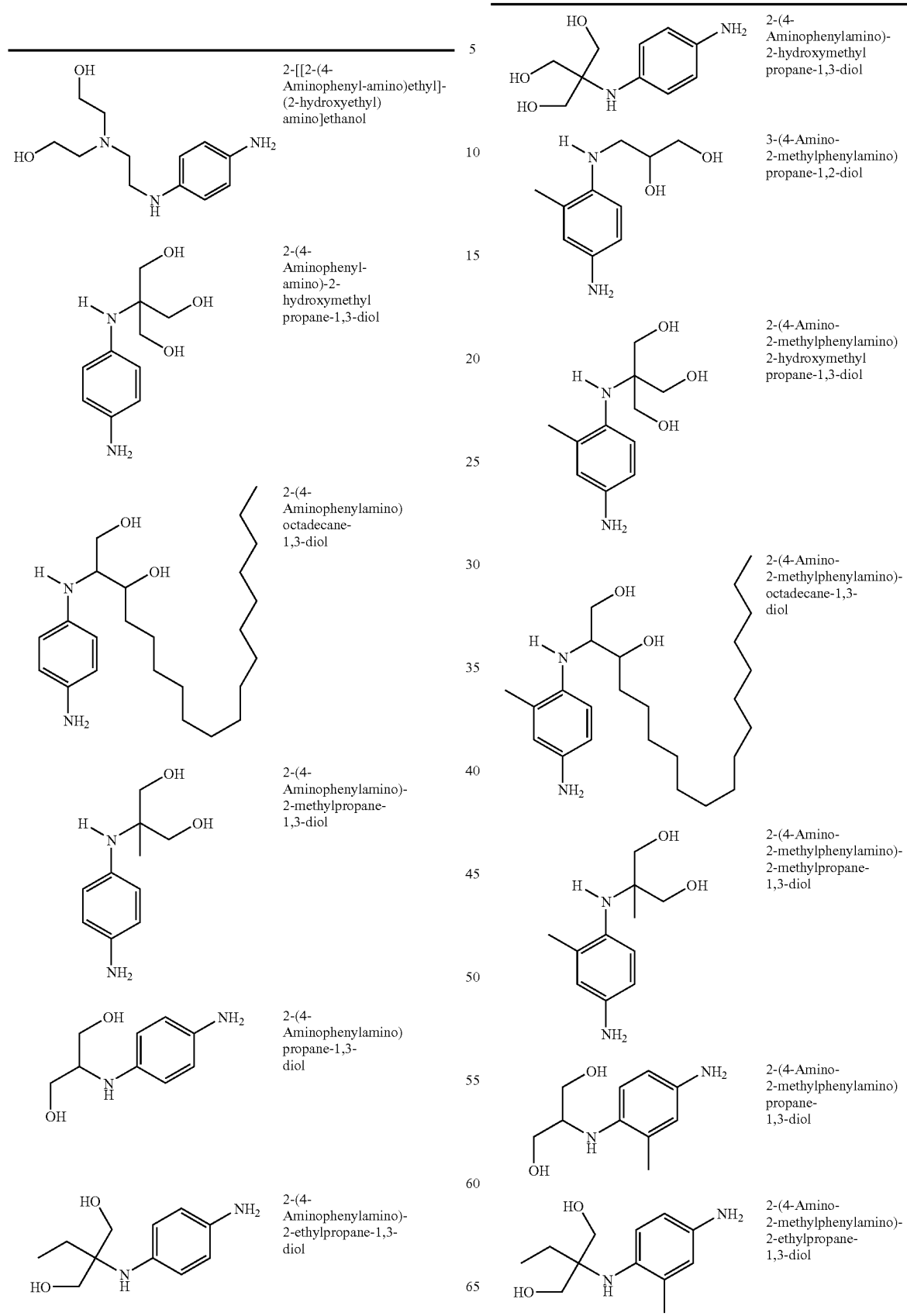

-continued

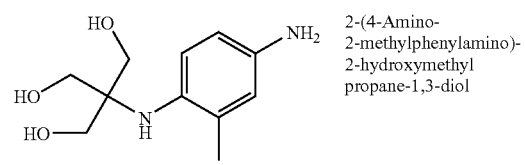
2-(4-Amino-2-methylphenylamino)-2-hydroxymethyl propane-1,3-diol

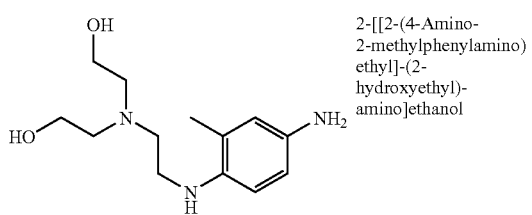
2-[[2-(4-Amino-2-methylphenylamino)ethyl]-(2-hydroxyethyl)-amino]ethanol

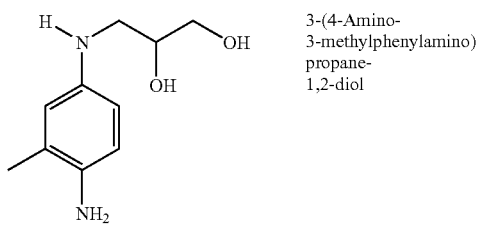
3-(4-Amino-3-methylphenylamino)propane-1,2-diol

2-(4-Amino-3-methylphenylamino)-2-hydroxymethyl propane-1,3-diol

2-(4-Amino-3-methylphenylamino)-octadecane-1,3-diol

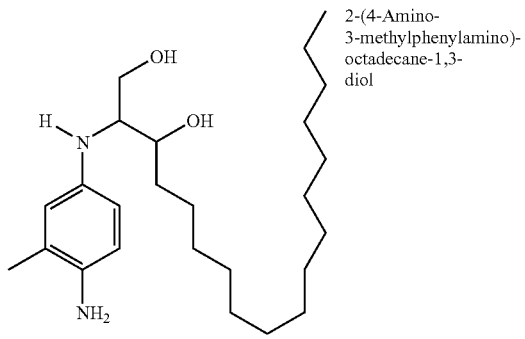

2-(4-Amino-3-methylphenylamino)-2-methyl-propane-1,3-diol

-continued

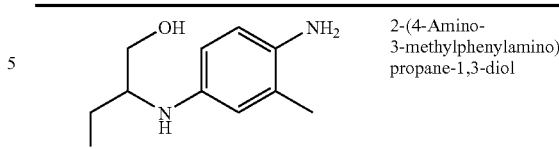
2-(4-Amino-3-methylphenylamino) propane-1,3-diol

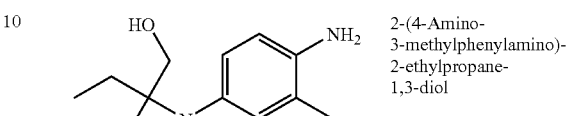
2-(4-Amino-3-methylphenylamino)-2-ethylpropane-1,3-diol

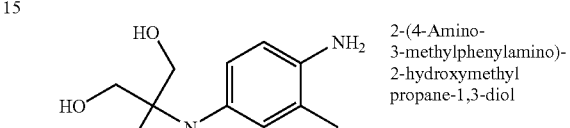
2-(4-Amino-3-methylphenylamino)-2-hydroxymethyl propane-1,3-diol

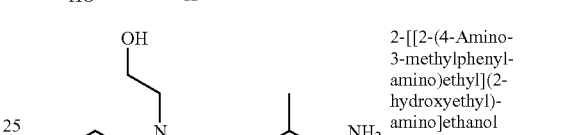
2-[[2-(4-Amino-3-methylphenyl-amino)ethyl](2-hydroxyethyl)-amino]ethanol

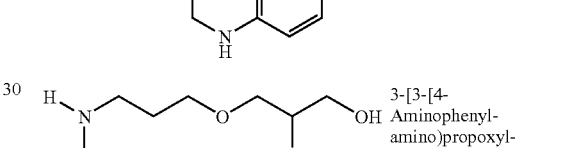
3-[3-[4-Aminophenyl-amino)propoxyl-propane-1,2-diol

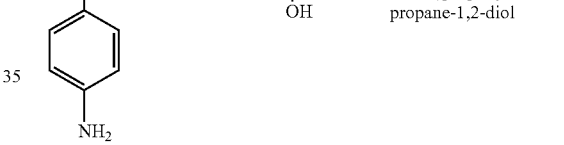
2-[[4-(4-Aminophenyl-amino)butyl]-(2-hydroxyethyl) amino]ethanol

The addition salts that may be used for the oxidation bases and the couplers can be chosen, for example, from acid addition salts such as the hydrochlorides, hydrobromides, sulfates, citrates, succinates, tartrates, lactates, tosylates, benzenesulfonates, phosphates, and acetates.

The compounds of formula (I) according to the present disclosure may be prepared, for example, according to methods that comprise the following steps:

nucleophilic substitution of the halogen in the para position of the para-halonitrobenzene with a primary amine of formula $RNH_2$ in the presence of a base, R being defined as above;

reduction of the nitro functional group of the compound obtained in the preceding step into an amine functional group, to obtain the compound of formula (I).

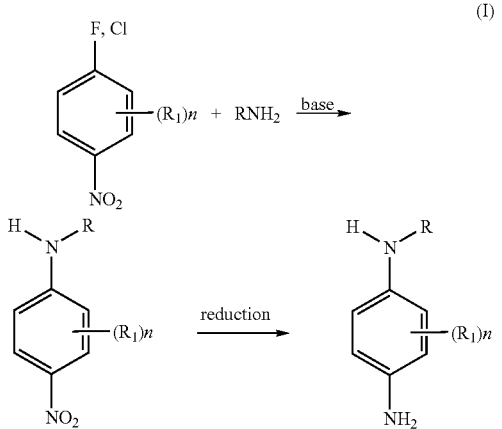

The first step of the synthesis is described in the scientific reviews *Synthesis* 1990 (12), 1147-1148 and *Synth. Commun.* 1990, 20 (22), 3537-3545.

The second step is an art-recognized reduction step, which can be performed, for example, by a hydrogenation reaction via heterogeneous catalysis in the presence of Pd/C, Pd(II)/C or Raney Ni, or by a reduction reaction with a metal, for example with zinc, iron, tin, etc. (*Advanced Organic Chemistry*, 4th edition, 1992, J. March, Wiley Interscience; *Reduction in Organic Chemistry*, M. Hudlicky, 1983, Ellis Honwood series Chemical Science).

The present disclosure also relates to the nitro compounds of formula (II) and processes for preparing the secondary para-phenylenediamine compounds of formula (I), which comprise a reduction of the corresponding nitro compound of formula (II).

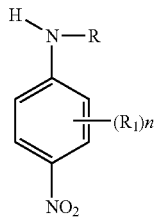

(II)

The present disclosure also relates to the use of compounds of formula (I), and the addition salts thereof:

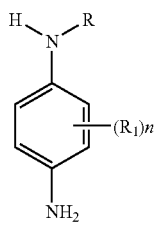

(I)

wherein:
R is chosen from linear and branched $C_2$-$C_{18}$ alkyl radicals comprising from 2 to 4 hydroxyl groups, wherein the alkyl radical are unsubstituted or substituted with at least one entity chosen from amino, mono($C_1$-$C_{15}$)alkylamino, di($C_1$-$C_{15}$)alkylamino, ($C_1$-$C_{15}$)alkylcarbonyl, amido, mono($C_1$-$C_{15}$)alkylaminocarbonyl, and di($C_1$-$C_{15}$)alkylaminocarbonyl groups, and wherein the alkyl radicals may be optionally interrupted with at least one heteroatom chosen from oxygen and nitrogen;

$R_1$ is chosen from hydrogen atoms, C-$C_{15}$ alkyl radicals, $C_1$-$C_{15}$ alkoxy radicals, hydroxy(($C_1$-$C_{15}$)alkoxy) radicals, ($C_1$-$C_{15}$)alkoxy($C_1$-$C_{15}$)alkyl radicals, $C_1$-$C_{15}$ monohydroxyalkyl radicals, $C_1$-$C_{15}$ polyhydroxyalkyl radicals, and halogen atoms;

n is an integer ranging from 1 to 4;

wherein the compound is not N-(2,3-dihydroxypropyl)-para-phenylenediamine.

The present disclosure also relates to cosmetic compositions for dyeing fibers, for example keratin fibers such as hair, comprising, in a medium that is suitable for dyeing, at least one compound of formula (I), and the addition salts thereof:

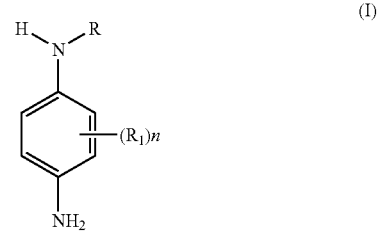

(I)

wherein:
R is chosen from linear and branched $C_2$-$C_{18}$ alkyl radicals comprising from 2 to 4 hydroxyl groups, wherein the alkyl radicals are unsubstituted or substituted with at least one entity chosen from amino, mono($C_1$-$C_{15}$)alkylamino, di($C_1$-$C_{15}$)alkylamino, ($C_1$-$C_{15}$)alkylcarbonyl, amido, mono($C_1$-$C_{15}$)alkylaminocarbonyl, and di($C_1$-$C_{15}$)alkylaminocarbonyl groups, and wherein the alkyl radicals are optionally interrupted with at least one heteroatom chosen from oxygen and nitrogen;

$R_1$ is chosen from hydrogen, $C_1$-$C_{15}$ alkyl radicals, $C_1$-$C_{15}$ alkoxy radicals, hydroxy(($C_1$-$C_{15}$)alkoxy) radicals, ($C_1$-$C_{15}$)alkoxy($C_1$-$C_{15}$)alkyl radicals, $C_1$-$C_{15}$ monohydroxyalkyl radicals, $C_1$-$C_{15}$ polyhydroxyalkyl radicals, and halogen atoms;

n is an integer ranging from 1 to 4;

wherein the compound is not N-(2,3-dihydroxypropyl)-para-phenylenediamine.

In one embodiment, the group R of formula (I) is chosen from linear and branched $C_2$-$C_{18}$ alkyl radicals comprising from 2 to 4 hydroxyl groups, wherein the alkyl radical may be optionally interrupted with at least one heteroatom chosen from oxygen and nitrogen; and the group $R_1$ of formula (I) is chosen from hydrogen, $C_1$-$C_6$ alkyl radicals, and $C_1$-$C_6$ alkoxy radicals.

The compounds of formula (I) may be chosen from:

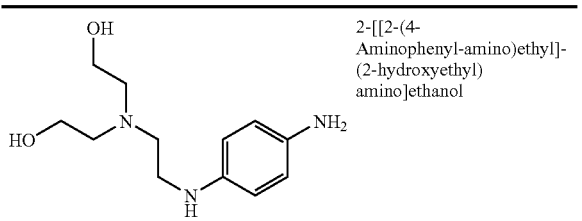
2-[[2-(4-Aminophenyl-amino)ethyl]-(2-hydroxyethyl)amino]ethanol

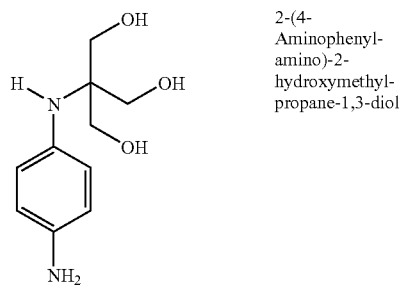
2-(4-Aminophenyl-amino)-2-hydroxymethyl-propane-1,3-diol

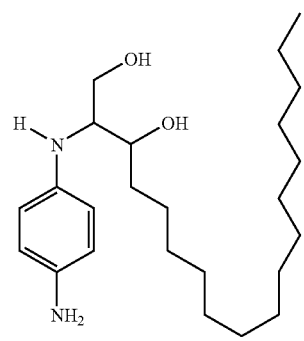
2-(4-Aminophenylamino)octadecane-1,3-diol

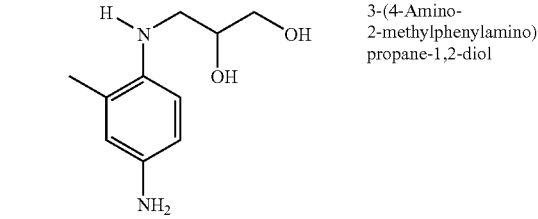
3-(4-Amino-2-methylphenylamino)propane-1,2-diol

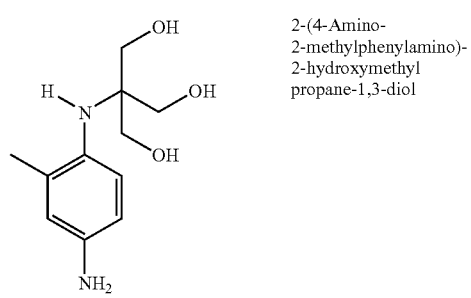
2-(4-Amino-2-methylphenylamino)-2-hydroxymethyl propane-1,3-diol

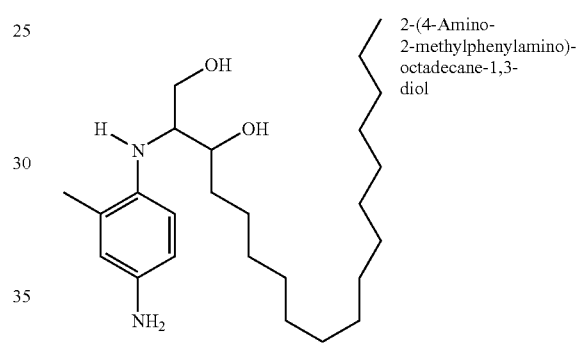
2-(4-Amino-2-methylphenylamino)octadecane-1,3-diol

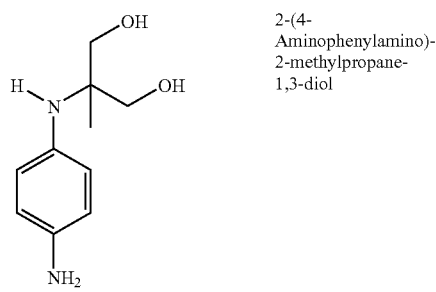
2-(4-Aminophenylamino)-2-methylpropane-1,3-diol

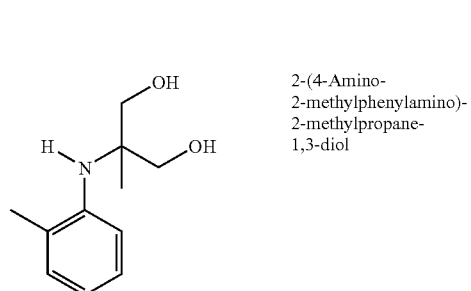
2-(4-Amino-2-methylphenylamino)-2-methylpropane-1,3-diol

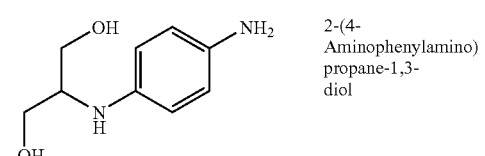
2-(4-Aminophenylamino)propane-1,3-diol

2-(4-Amino-2-methylphenylamino)propane-1,3-diol

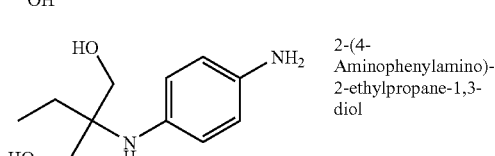
2-(4-Aminophenylamino)-2-ethylpropane-1,3-diol

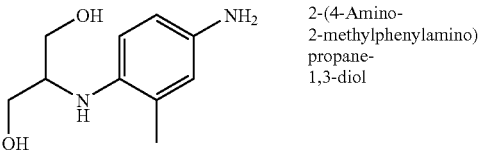
2-(4-Amino-2-methylphenylamino)-2-ethylpropane-1,3-diol

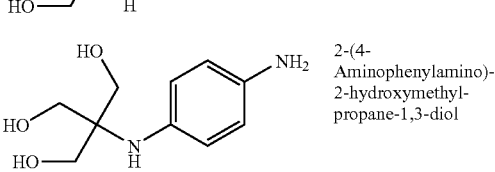
2-(4-Aminophenylamino)-2-hydroxymethyl-propane-1,3-diol

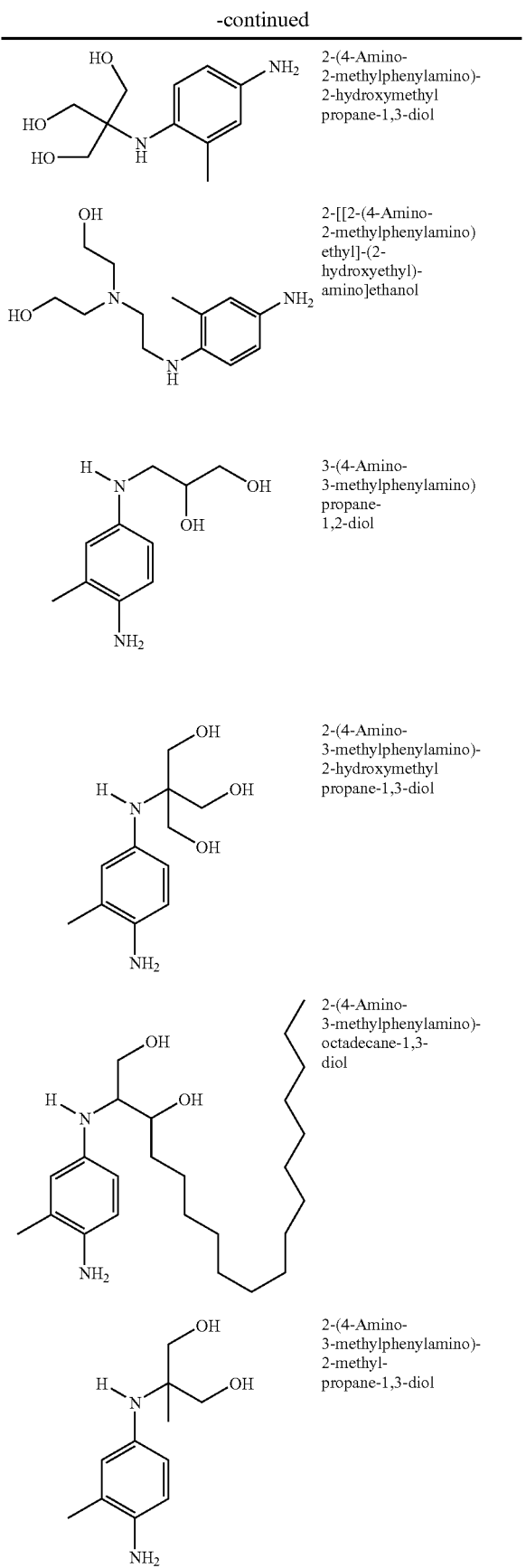
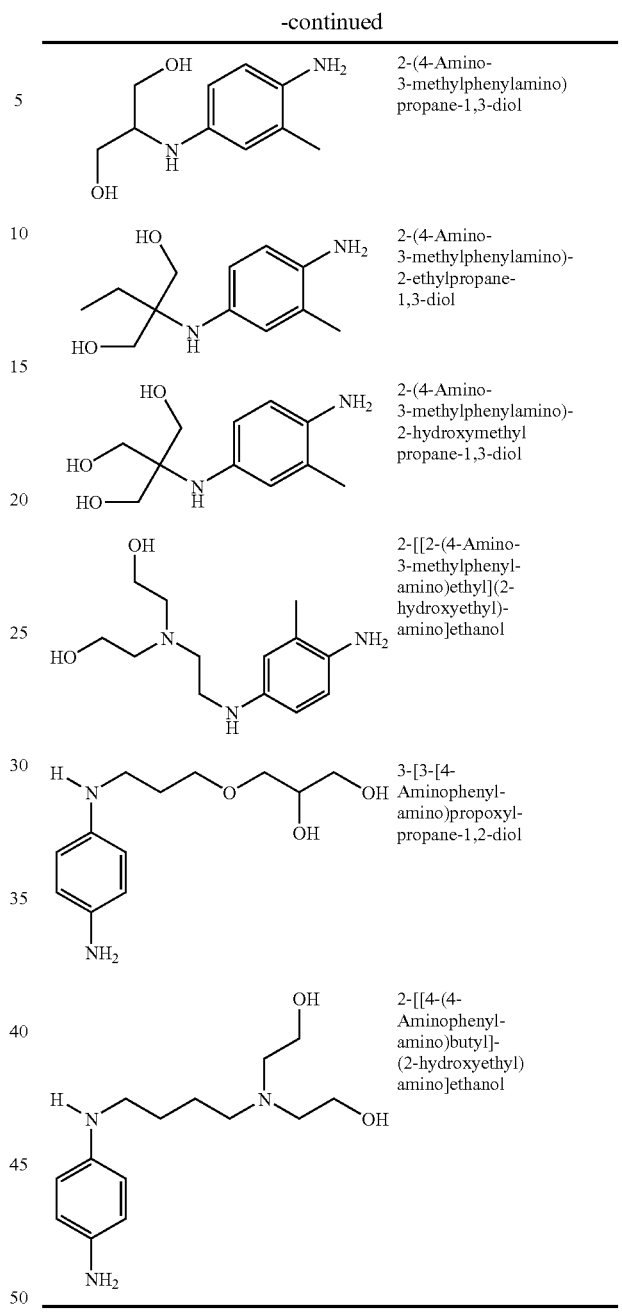

The addition salts that may be used for the oxidation bases and the couplers can be chosen, for example, from acid addition salts such as the hydrochlorides, hydrobromides, sulfates, citrates, succinates, tartrates, lactates, tosylates, benzenesulfonates, phosphates, and acetates.

For example, the compound of formula (I) may be present in an amount ranging from 0.0001% to 20%, such as from 0.005% to 6% by weight, relative to the total weight of the composition.

The medium that is suitable for dyeing may comprise water or may comprise water and at least one organic solvent, chosen for instance from branched and unbranched $C_1$-$C_4$ lower alcohols, such as ethanol and isopropanol; polyols and polyol ethers, for instance 2-butoxyethanol, propylene glycol, propylene glycol monomethyl ether, diethylene glycol monomethyl ether, diethylene glycol monoethyl ether, and glycerol; aromatic alcohols, for instance benzyl alcohol and phenoxyethanol; and mixtures thereof.

When present, the at least one organic solvent may be in an amount ranging from 1% to 40% by weight, such as from 5% to 30% by weight, relative to the total weight of the dye composition.

The cosmetic compositions may comprise at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents, opacifiers, vitamins, and provitamins.

When present, each adjuvant may be in an amount ranging from 0.01% to 20% by weight, relative to the weight of the composition.

The compositions according to the present disclosure may also comprise at least one oxidation coupler.

Among the oxidation couplers that may used, non-limiting mention may be made of meta-phenylenediamines, meta-aminophenols, meta-diphenols, naphthalene-based couplers, heterocyclic couplers, and the addition salts thereof.

Non-limiting examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-1-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6dimethoxypyridine, 1-N-(β-hydroxyethyl)amino-3,4-methylenedioxybenzene, 2,6-bis(β-hydroxyethylamino)toluene, and the addition salts thereof.

When present, the at least one oxidation coupler may be in an amount ranging from 0.0001% to 20%, for example from 0.005% to 6% by weight, relative to the total weight of the composition.

The compositions according to the present disclosure may also comprise additional oxidation bases other than compounds of formula (I).

The oxidation bases may be chosen, for example, from para-phenylenediamines, bis(phenyl)alkylenediamines, para-aminophenols, ortho-amino phenols, heterocyclic bases, and the addition salts thereof.

Among the para-phenylenediamines, non-limiting mention may be made, by way of example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methyl-aniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-p-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(D-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, 6-(4-aminophenylamino)hexan-1-ol, and the acid addition salts thereof.

Among the para-phenylenediamines mentioned above, further non-limiting examples include para-phenylenediamine, para-tolylenediamine, 2-isopropyl-para-phenylenediamine, 2-O-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-O-acetylaminoethyloxy-para-phenylenediamine, and the acid addition salts thereof.

Among the bis(phenyl)alkylenediamines, non-limiting mention may be made, by way of example, of N,N'-bis(β-hydroxyethyl)-N,N'-bis(4'-aminophenyl)-1-3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-amino-phenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diamino-phenoxy)-3,6-dioxaoctane, and the acid addition salts thereof.

Among the para-aminophenols, non-limiting mention may be made, by way of example, of para-aminophenol, 4-amino-2-methylphenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2,6-dichlorophenol, 4-amino-6[((5'-amino-2'-hydroxy-3'-methyl)phenyl)methyl]-2-methylphenol, bis(5'-amino-2'-hydroxy)phenylmethane, and the acid addition salts thereof.

Among the ortho-aminophenols, non-limiting mention may be made, by way of example, of 2-aminophenol, 2-amino-5-methylphenol, 2-amino-6-methylphenol, 5-acetamido-2-aminophenol, and the acid addition salts thereof.

Among the heterocyclic bases, non-limiting mention may be made, by way of example, of pyridine derivatives, pyrimidine derivatives, and pyrazole derivatives.

Among the pyridine derivatives, non-limiting mention may be made of the compounds described, for example, in British Patent Nos. GB 1,026,978 and GB 1,153,196, such as 2,5-diaminopyridine, 2-(4-methoxyphenyl)amino-3-aminopyridine, 3,4-diaminopyridine, and the acid addition salts thereof.

Other pyridine oxidation bases that may be used in the present disclosure include, but are not limited to, the 3-aminopyrazolo[1,5-a]pyridine oxidation bases and the addition salts thereof described, for example, in French Patent Application No. FR 2,801,308. Non-limiting examples that may be mentioned include pyrazolo[1,5-a]pyrid-3-ylamine; 2-acetylaminopyrazolo[1,5-a]pyrid-3-ylamine; 2-morpholin-4-ylpyrazolo-[1,5-a]pyrid-3-ylamine; 3-aminopyrazolo[1,5-a]pyridin-2-carboxylic acid; 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2-(3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyrid-3,7-diamine; 7-morpholin-4-ylpyrazolo-[1,5-a]pyrid-3- ylamine; pyrazolo[1,5-a]pyrid-3,5-diamine; 5-morpholin-4-ylpyrazolo[1,5-a]pyrid-3-ylamine; 2-[(3-aminopyrazolo[1,5-a]pyrid-5-yl)-(2-hydroxyethyl)amino]ethanol; 2-[(3-aminopyrazolo[1,5-a]pyrid-7-yl)-(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyridine-6-ol; 3-aminopyrazolo[1,5-a]pyrid-7-ol; and the acid addition salts thereof.

Among the pyrimidine derivatives, non-limiting mention may be made of the compounds described, for example, in German Patent No. DE 2,359,399; Japanese Patent Nos. JP 88-169,571 and JP 05,63,124; European Patent No. EP 0,770,375; and International Patent Publication No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, the addition salts thereof, and the tautomeric forms thereof, when a tautomeric equilibrium exists.

Among the pyrazole derivatives, non-limiting mention may be made of the compounds described in German Patent Nos. DE 3,843,892 and DE 4,133,957, International Patent Publication Nos. WO 94/08969 and WO 94/08970, French Patent Application No. FR-A-2,733,749, and German Patent Application No. DE 195,43,988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole,1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

When present, the at least one oxidation base may be in an amount ranging from 0.0001% to 20% by weight, for example from 0.005% to 6% by weight, relative to the total weight of the composition.

The addition salts that may be used for the oxidation bases and the couplers can be chosen, for example, from acid addition salts such as the hydrochlorides, hydrobromides, sulfates, citrates, succinates, tartrates, lactates, tosylates, benzenesulfonates, phosphates, and acetates.

The dye compositions in accordance with the present disclosure may also comprise at least one direct dye, which may be chosen, for example, from neutral, acidic, and cationic nitrobenzene dyes; neutral, acidic, and cationic azo direct dyes; neutral, acidic, and cationic quinone dyes, such as anthraquinone direct dyes; azine direct dyes; methine, azomethine, triarylmethane, and indoamine direct dyes; and natural direct dyes. In one embodiment, the compositions according to the present disclosure comprise at least one dye chosen from cationic direct dyes and natural direct dyes.

Among the cationic direct dyes that may be used according to the present disclosure, non-limiting mention may be made of the cationic azo direct dyes described in International Patent Publications WO 95/15144 and WO 95/01772, and European Patent Application EP 714,954.

Among these compounds, further non-limiting mention may be made of the following dyes:

1,3-dimethyl-2-[[4-(dimethylamino)phenyl]azo]-1H-imidazolium chloride;

1,3-dimethyl-2-[(4-aminophenyl)azo]-1H-imidazolium chloride; and 1-methyl-4-[(methylphenylhydrazono)methyl]pyridinium methyl sulfate.

Among the natural direct dyes that may be used according to the present disclosure, non-limiting mention may be made of lawsone, juglone, alizarin, purpurin, carminic acid, kermesic acid, purpurogallin, protocatechaldehyde, indigo, isatin, curcumin, spinulosin, and apigenidin. It is also possible to use extracts and decoctions comprising these natural dyes, for example henna-based poultices and extracts.

When present, the at least one direct dye may be in an amount ranging from 0.001% to 20% by weight, for example from 0.005% to 10% by weight, relative to the total weight of the ready-to-use composition.

A person skilled in the art will take care to select the adjuvant(s), additional oxidation dye precursor(s), oxidation coupler(s), and direct dye(s) such that the beneficial properties intrinsically associated with the oxidation dye compositions in accordance with the present disclosure are not, or are not substantially, adversely affected by the envisaged addition(s).

Ready-to-use dye compositions may be obtained by adding at least one oxidizing agent conventionally used for the oxidation dyeing of keratin fibers such as, for example, hydrogen peroxide; urea peroxide; alkali metal bromates; persalts such as perborates and persulfates; peracids; and oxidase enzymes, among which non-limiting mention may be made of peroxidases, two-electron oxidoreductases such as uricases, and four-electron oxygenases, for instance laccases. In one embodiment, the ready-to-use dye compositions comprise hydrogen peroxide.

The pH of the dye compositions in accordance with the present disclosure may range from 3 to 12, for example from 5 to 11. It may be adjusted to the desired value using acidifying or basifying agents usually used in the dyeing of keratin fibers, or alternatively using standard buffer systems.

Among the acidifying agents that may be used, non-limiting mention may be made, for example, of mineral and organic acids other than carboxylic diacids, for instance hydrochloric acid, orthophosphoric acid, sulfuric acid, carboxylic acids, such as acetic acid, tartaric acid, citric acid and lactic acid, and sulfonic acids.

Among the basifying agents that may be used, non-limiting mention may be made, for example, of aqueous ammonia, alkali metal carbonates, alkanolamines such as monoethanolamine, diethanolamine, triethanolamine, and derivatives thereof, sodium hydroxide, potassium hydroxide, and the compounds of formula (III):

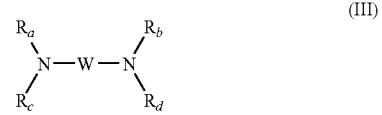

wherein:

W is chosen from propylene residues optionally substituted with a hydroxyl group or a $C_1$-$C_4$ alkyl radical; and $R_a$, $R_b$, $R_c$, and $R_d$, which may be identical or different, are chosen from hydrogen, and $C_1$-$C_4$ alkyl and $C_1$-$C_4$ hydroxyalkyl radicals.

The dye compositions according to the present disclosure may be in various forms, such as in the form of liquids, creams or gels, or in any other form that is suitable for dyeing keratin fibers, such as hair.

The present disclosure also relates to processes in which the compositions as defined above are applied to the fibers and the color is developed using an oxidizing agent. The color may be developed at acidic, neutral or alkaline pH. The oxidizing agent may be added to the compositions of the present disclosure just at the time of use. It may also be used starting with an oxidizing composition comprising it, which is applied simultaneously with or sequentially to the fibers at the time of application of the dye compositions of the present disclosure.

In one embodiment, a composition in accordance with the present disclosure is mixed, for example, at the time of use, with a composition comprising, in a medium that is suitable for dyeing, at least one oxidizing agent, this oxidizing agent being present in an amount that is sufficient to develop a coloration. The mixture obtained is then applied to keratin fibers. After leaving it to act for a period of time ranging from 3 to 50 minutes, for example from 5 to 30 minutes, the keratin fibers are rinsed, washed with shampoo, rinsed again, and then dried.

The oxidizing compositions may comprise various adjuvants conventionally used in hair dye compositions and as defined above.

The pH of the oxidizing compositions comprising the oxidizing agent may be such that, after mixing with a dye composition in accordance with the present disclosure, the pH of the resulting composition applied to the keratin fibers ranges, for example, from 3 to 12, such as from 5 to 11. It may be adjusted to the desired value by means of acidifying or basifying-agents usually used in the dyeing of keratin fibers and as defined above.

The ready-to-use compositions that are finally applied to the keratin fibers may be in various forms, such as in the form of liquids, creams or gels, or in any other form that is suitable for dyeing keratin fibers, for example hair.

The present disclosure also relates to the use of the cosmetic compositions described herein comprising, in a medium that is suitable for dyeing, at least one compound of formula (I) for dyeing fibers, for example keratin fibers such as hair.

The present disclosure also relates to multi-compartment devices or dyeing kits, in which at least one first compartment comprises at least one dye composition described herein and at least one second compartment comprises at least one oxidizing composition. This device may be equipped with a device for applying the desired mixture to the hair, such as the devices described in French Patent No. FR-2,586,913.

Using these kits, it may be possible to dye keratin fibers via processes that include mixing at least one dye composition in accordance with the present disclosure with at least one oxidizing agent as defined above, and applying the mixture obtained to the keratin fibers for a time that is sufficient to develop the desired coloration.

The present disclosure may be understood more clearly with the aid of the non-limiting examples that follow, which constitute various embodiments of the compositions according to the disclosure. Other than in the examples, or where otherwise indicated, all numbers expressing quantities of ingredients, reaction conditions, and so forth used in the specification and claims are to be understood as being modified in all instances by the term "about" Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements.

EXAMPLES

-A- Examples of Synthesis

Example 1

Synthesis of 2-(4-aminophenylamino)-2-methylpropane-1,3-diol Dihydrochloride (2)

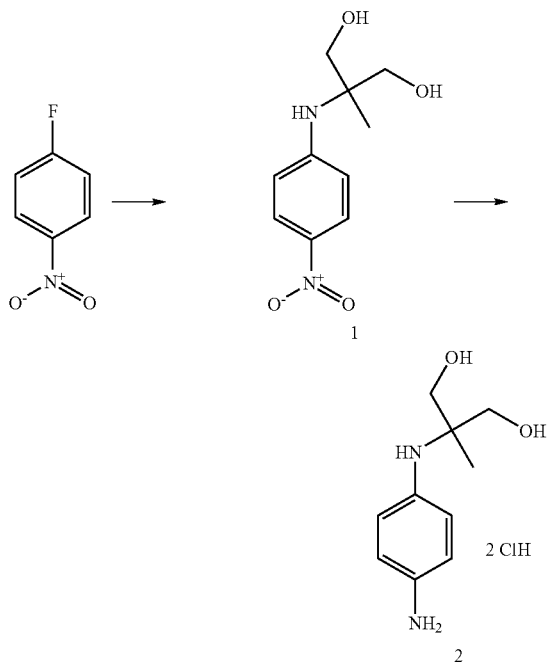

Step 1: Preparation of 2-methyl-2-(4-nitrophenylamino)propane-1,3-diol (1)

43 g of 2-amino-2-methyl-2,3-propanediol were melted at 120° C. and 21.15 g (0.15 mol) of 1-fluoro-4-nitrobenzene were then added. The mixture was heated at 180° C. for 1 hour.

When the reaction was complete, the medium was poured onto an ice/water mixture with vigorous stirring. A yellow precipitate formed, which was filtered off, washed with water and then dried to give 27.6 g of solid.

After recrystallization from ethanol, elemental analysis gave the following results:

|   | THEORY | FOUND |
|---|--------|-------|
| C | 53.09  | 53.13 |
| H | 6.24   | 6.28  |
| N | 12.38  | 12.34 |
| O | 28.29  | 28.37 |

Step 2: Preparation of 2-(4-phenylamino)methylpropane-1,3-diol Dihydrochloride (2)

22.6 g (0.1 mol) of 2-methyl-2-(4-nitrophenylamino)propane-1,3-diol (1) were placed in a mixture of alcohol, water, and cyclohexene in proportions of 67 ml/5 ml/46 ml. 10 g of 10% Pd/C catalyst were added and the mixture was refluxed for 2 hours. The medium was filtered while hot and the catalyst was washed with alcohol. The filtrate was concentrated to dryness and then taken up in alcohol. After cooling, 50 ml of 7N hydrochloric ethanol were added. The precipitate formed was filtered off, washed with alcohol, then with isopropyl ether, and finally with petroleum ether. After drying, 23.4 g of expected product were obtained.

After recrystallization, elemental analysis gave the following results:

|    | THEORY | FOUND |
|----|--------|-------|
| C  | 44.62  | 44.14 |
| H  | 6.74   | 6.77  |
| N  | 10.41  | 10.26 |
| O  | 11.89  | 12.49 |
| Cl | 26.34  | 26.10 |

The proton NMR and mass spectra were in accordance with the expected structure of the product.

Example 2

Synthesis of 2-(4-aminophenylamino)octadecane-1,3-diol Dihydrochloride (4)

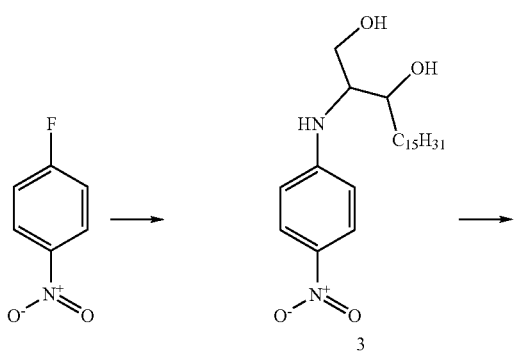

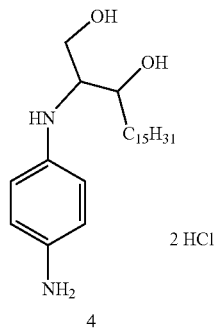

Step 1: Preparation of 2-(4-nitrophenylamino)octadecane-1,3-diol (3)

13 g (0.092 mol) of 4-fluoronitrobenzene, 30 g (0.099 mol) of 2-aminooctadecane-1,3-diol and 11 g (0.104 mol) of sodium carbonate were introduced into a 250 ml reactor equipped with a condenser. The reaction mixture was maintained at 120° C. for 3 hours. 200 ml of water were added slowly to the reaction medium, which was then poured into 500 ml of ice-cold water. The precipitate formed was filtered off on a sinter funnel and dried under vacuum at 50° C. in the presence of $P_2O_5$. After recrystallization twice from ethanol, 10 g of yellow powder were isolated.

|   | THEORY | FOUND |
|---|--------|-------|
| C | 68.21  | 68.26 |
| H | 10.02  | 10.16 |
| N | 6.63   | 6.46  |
| O | 15.14  | 14.47 |

Step 2: Preparation of 2-(4-aminophenylamino)octadecane-1,3-diol Dihydrochloride (4)

10 g (0.0237 mol) of 2-(4-nitrophenylamino)octadecane-1,3-diol (3) were suspended in 70 ml of ethanol in a 250 ml reactor equipped with a condenser. 6 g of 10% Pd/C containing 50% water and 60 ml of cyclohexene were added. The reaction mixture was refluxed for 2 hours. The resulting mixture was filtered while hot through Celite and then concentrated to half its volume. The medium was cooled to 5° C. with an ice bath, HCl gas was then bubbled through slowly and the product precipitated out. This product was filtered off on a sinter funnel and then washed with a small amount of isopropyl ether. It was dried under vacuum in the presence of $P_2O_5$ at 50° C. 9.6 g of a white powder were obtained.

|    | THEORY | FOUND |
|----|--------|-------|
| C  | 61.92  | 61.85 |
| H  | 9.96   | 10.05 |
| N  | 6.02   | 5.93  |
| O  | 6.87   | 6.86  |
| Cl | 15.23  | 15.13 |

The proton NMR and mass spectra were in accordance with the expected structure of the product.

Example 3

Synthesis of 2-(4-aminophenylamino)-2-hydroxymethylpropane-1,3-diol (6)

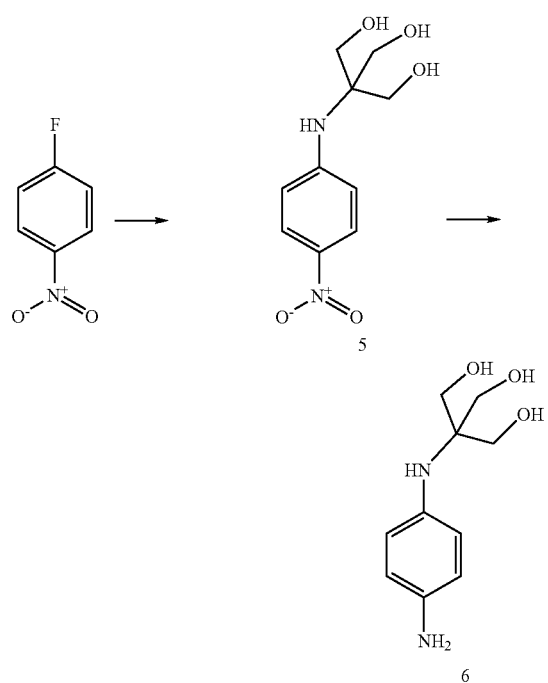

Step 1: Preparation of 2-hydroxymethyl-2-(4-nitrophenylamino)propane-1,3-diol (5)

43 g of tris(hydroxymethylamino)methane were melted at 165° C. and 21.15 g (0.15 mol) of 1-fluoro-4-nitrobenzene were then added at 170-180° C. The mixture was stirred at 170° C. for 30 minutes and then heated at 190° C. for 1 hour. When the reaction was complete, the medium was poured onto an ice/water mixture with vigorous stirring. The yellow precipitate formed was filtered off and washed with water and 3 times with alcohol. After recrystallization from ethanol, 14 g of expected product were isolated.

The elemental analysis gave the following results:

|   | THEORY | FOUND |
|---|--------|-------|
| C | 49.59  | 49.78 |
| H | 5.83   | 5.80  |
| N | 11.56  | 11.20 |
| O | 33.02  | 32.82 |

Step 2: Preparation of 2-(4-aminophenylamino)-2-hydroxymethylpropane-1,3-diol (6)

7.3 g (0.03 mol) of 2-hydroxymethyl-2-(4-nitrophenylamino)propane-1,3-diol (5) were placed in a mixture of alcohol, water, and cyclohexene in proportions of 30 ml/15 ml/3 ml. 3 g of 10% Pd/C catalyst were added and the mixture was refluxed for 2 hours until decolorized. The medium was filtered while hot and the catalyst was washed with alcohol. The filtrate was concentrated to dryness and then taken up in 10 ml of ethanol, and the precipitate formed was filtered off and washed with alcohol and then with isopropyl ether. After drying, 3.7 g of a white powder were obtained, the elemental analysis of which gave the following results:

|   | THEORY | FOUND |
|---|--------|-------|
| C | 56.59  | 56.54 |
| H | 7.60   | 7.60  |
| N | 13.20  | 13.20 |
| O | 22.61  | 22.81 |

The proton NMR and mass spectra were in accordance with the expected structure of the product.

Example 4

Synthesis of 3-(4-amino-2-methylphenylamino)propane-1,2-diol Dihydrochloride (8)

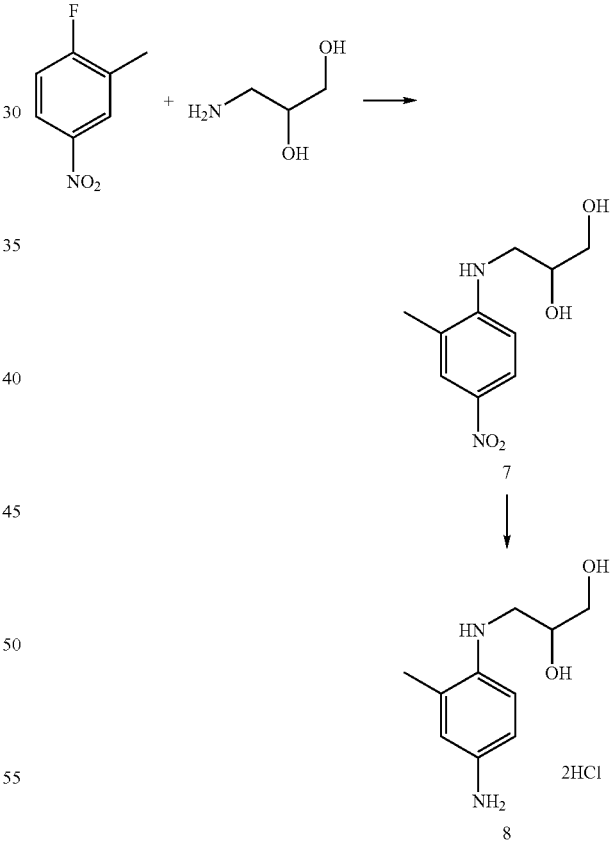

Step 1: Synthesis of 3-(4-nitro-2-methylphenylamino)propane-1,2-diol (7)

2 g of 2-fluoro-5-nitrotoluene were added to a solution of 20 ml of N-methylpyrrolidinone, 1.4 g of 2,3-dihydroxy-1-propylamine, and 2.14 g of $K_2CO_3$. The reaction medium was heated at 60° C. for 15 hours and, after cooling to room temperature, was poured into a water/ice mixture. A yellow precipitate formed, which was filtered off, reslurried in water and then dried over $P_2O_5$. 2 g of 3-(4-nitro-2-methylphenylamino)propane-1,2-diol (7) were obtained.

Step 2: Synthesis of
3-(4-amino-2-methylphenylamino)propane-1,2-diol
Dihydrochloride (8)

The 3-(4-nitro-2-methylphenylamino)propane-1,2-diol (7) obtained above was reduced with a boiling zinc/ammonium chloride/water/ethanol mixture. The corresponding amine was isolated in dihydrochloride form.

The proton NMR and mass spectra were in accordance with the expected structure of the product.

Example 5

Synthesis of
3-(4-amino-3-methylphenylamino)propane-1,2-diol
Dihydrochloride (10)

phase was then concentrated under vacuum. 0.28 g of 3-(4-nitro-3-methylphenylamino)propane-1,2-diol (9) was obtained.

Step 2: Synthesis of
3-(4-amino-3-methylphenylamino)propane-1,2-diol
Dihydrochloride (10)

The 3-(4-nitro-3-methylphenylamino)propane-1,2-diol (9) obtained above was reduced with a boiling zinc/ammonium chloride/water/ethanol mixture. The corresponding amine was isolated in dihydrochloride form.

The proton NMR and mass spectra were in accordance with the expected structure of the product.

Example 6

Synthesis of
2-(4-amino-3-methylphenylamino)propane-1,3-diol
Dihydrochloride (12)

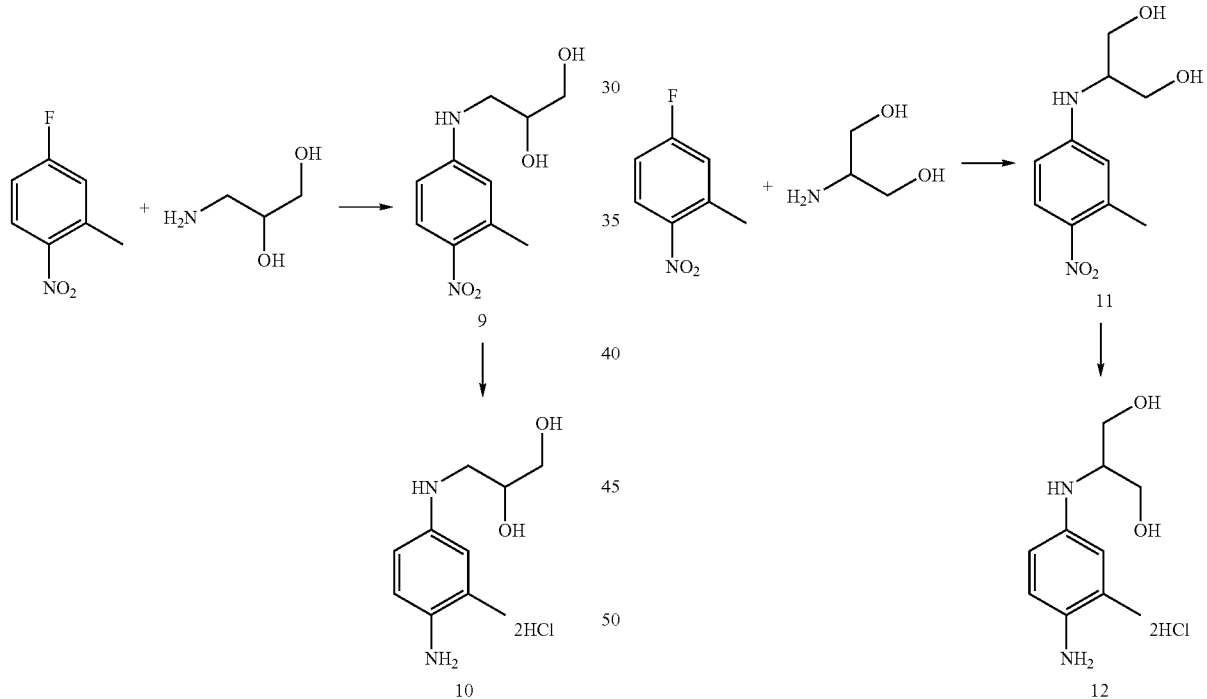

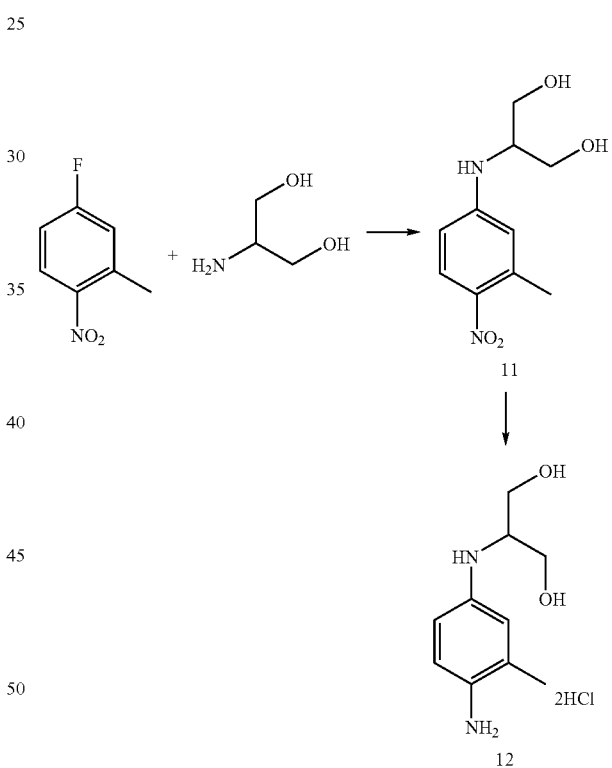

Step 1: Synthesis of
3-(4-nitro-3-methylphenylamino)propane-1,2-diol
(9)

2 g of 5-fluoro-2-nitrotoluene were added to a solution of 20 ml of N-methylpyrrolidinone, 1.41 g of 3-amino-1,2-propanediol, and 1.57 g of triethylamine. The reaction medium was heated at 60° C. for 10 hours and, after cooling to room temperature, was poured into a water/ice mixture. The resulting medium was extracted with ethyl acetate and the organic Step 1: Synthesis of
2-(4-nitro-3-methylphenylamino)propane-1,3-diol
(11)

2 g of 5-fluoro-2-nitrotoluene were added to a solution of 20 ml of N-methylpyrrolidinone, 1.4 g of 2-amino-1,3-propanediol, and 1.57 g of triethylamine. The reaction medium was heated at 60° C. for 10 hours and, after cooling to room temperature, was poured into a water/ice mixture. The resulting medium was extracted with ethyl acetate and the organic phase was then concentrated under vacuum. 1.45 g of 2-(4-nitro-3-methylphenylamino)propane-1,3-diol (11) were obtained.

Step 2: Synthesis of 2-(4-amino-3-methylphenylamino)propane-1,3-diol Dihydrochloride (12)

The 2-(4-nitro-3-methylphenylamino)propane-1,3-diol (11) obtained above was reduced with a boiling zinc/ammonium chloride/water/ethanol mixture. The corresponding amine was isolated in dihydrochloride form.

The proton NMR and mass spectra were in accordance with the expected structure of the product.

Example 7

Synthesis of 2-(4-amino-2-methylphenylamino)propane-1.3-diol Dihydrochloride (14)

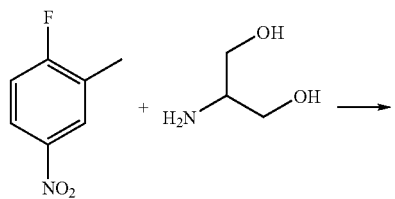

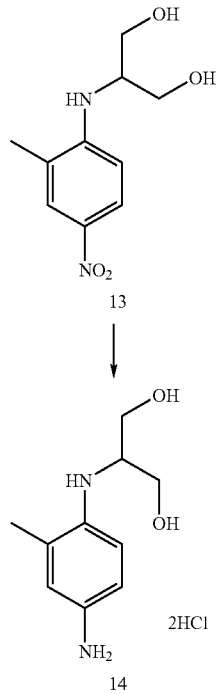

Step 1: Synthesis of 2-(4-nitro-2-methylphenylamino)propane-1,3-diol (13)

2 g of 2-fluoro-5-nitrotoluene were added to a solution of 20 ml of N-methylpyrrolidinone, 1.4 g of 2-amino-1,3-propanediol, and 1.57 g of triethylamine. The reaction medium was heated at 60° C. for 10 hours and, after cooling to room temperature, was poured into a water/ice mixture. The resulting medium was extracted with ethyl acetate and the organic phase was then concentrated under vacuum. 0.32 g of 2-(4-nitro-2-methylphenylamino)propane-1,3-diol (13) was obtained.

Step 2: Synthesis of 2-(4-amino-2-methylphenylamino)propane-1,3-diol Dihydrochloride (14)

The 2-(4-nitro-2-methylphenylamino)propane-1,3-diol (13) obtained above was reduced with a boiling zinc/ammonium chloride/water/ethanol mixture. The corresponding amine was isolated in dihydrochloride form.

The proton NMR and mass spectra were in accordance with the expected structure of the product.

Example 8

Synthesis of 2-(4-aminophenylamino)propane-1,3-diol Dihydrochloride (16)

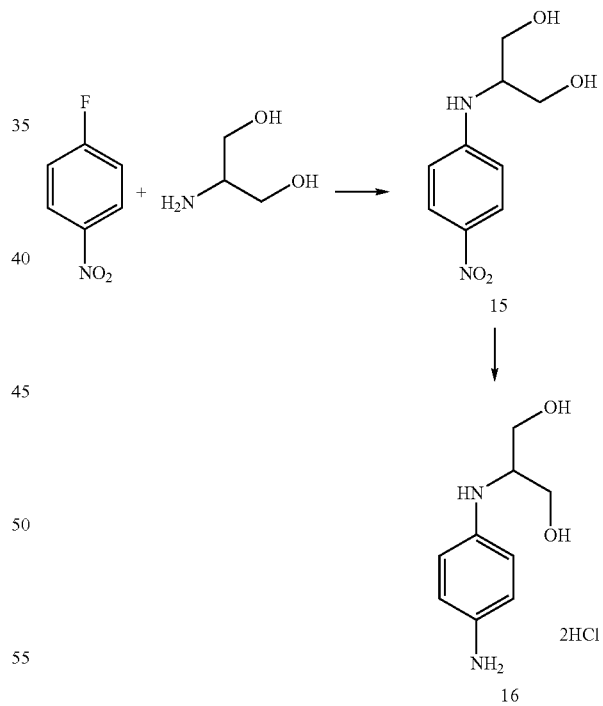

Step 1: Synthesis of 2-(4-nitrophenylamino)propane-1,3-diol (15)

2 g of para-fluoronitrobenzene were added to a solution of 20 ml of N-methylpyrrolidinone, 1.55 g of 2-amino-1,3-propanediol, and 2.35 g of $K_2CO_3$. The reaction medium was heated at 60° C. for 15 hours and, after cooling to room temperature, was poured-into a water/ice mixture. A yellow precipitate formed, which was filtered off, reslurried in water, and then dried over $P_2O_5$. 0.1 g of 2-(4-nitrophenylamino)propane-1,3-diol (15) was obtained after purification on a column of silica.

Step 2: Synthesis of 2-(4-aminophenylamino)propane-1,3-diol Dihydrochloride (16)

The 2-(4-nitrophenylamino)propane-1,3-diol (15) obtained above was reduced with a boiling zinc/ammonium chloride/water/ethanol mixture. The corresponding amine was isolated in dihydrochloride form.

The proton NMR and mass spectra were in accordance with the expected structure of the product.

Example 9

Synthesis of 2-[[2-(4-amino-2-methylphenylamino)ethyl]-(2-hydroxyethyl)amino]ethanol Dihydrochloride (18)

The reaction medium was heated at 80° C. for 10 hours and, after cooling to room temperature, was poured into a water/ice mixture. The resulting medium was extracted with ethyl acetate and the organic phase was then concentrated under vacuum. 1.5 g of 2[[2-(4-nitro-2-methylphenylamino)ethyl]-(2-hydroxyethyl)amino]ethanol (17) were obtained.

Step 2: Synthesis of 2-[[2-(4-amino-2-methylphenylamino)ethyl]-(2-hydroxyethyl)amino]ethanol Dihydrochloride (18)

The 2-[[2-(4-nitro-2-methylphenylamino)ethyl]-(2-hydroxyethyl)amino]ethanol (17) obtained above was reduced with a boiling zinc/ammonium chloride/water/ethanol mixture. The corresponding amine was isolated in dihydrochloride form.

The proton NMR and mass spectra were in accordance with the expected structure of the product.

Example 10

Synthesis of 2-[[2-(4-aminophenylamino)ethyl]-(2-hydroxyethyl)amino]ethanol Dihydrochloride (20)

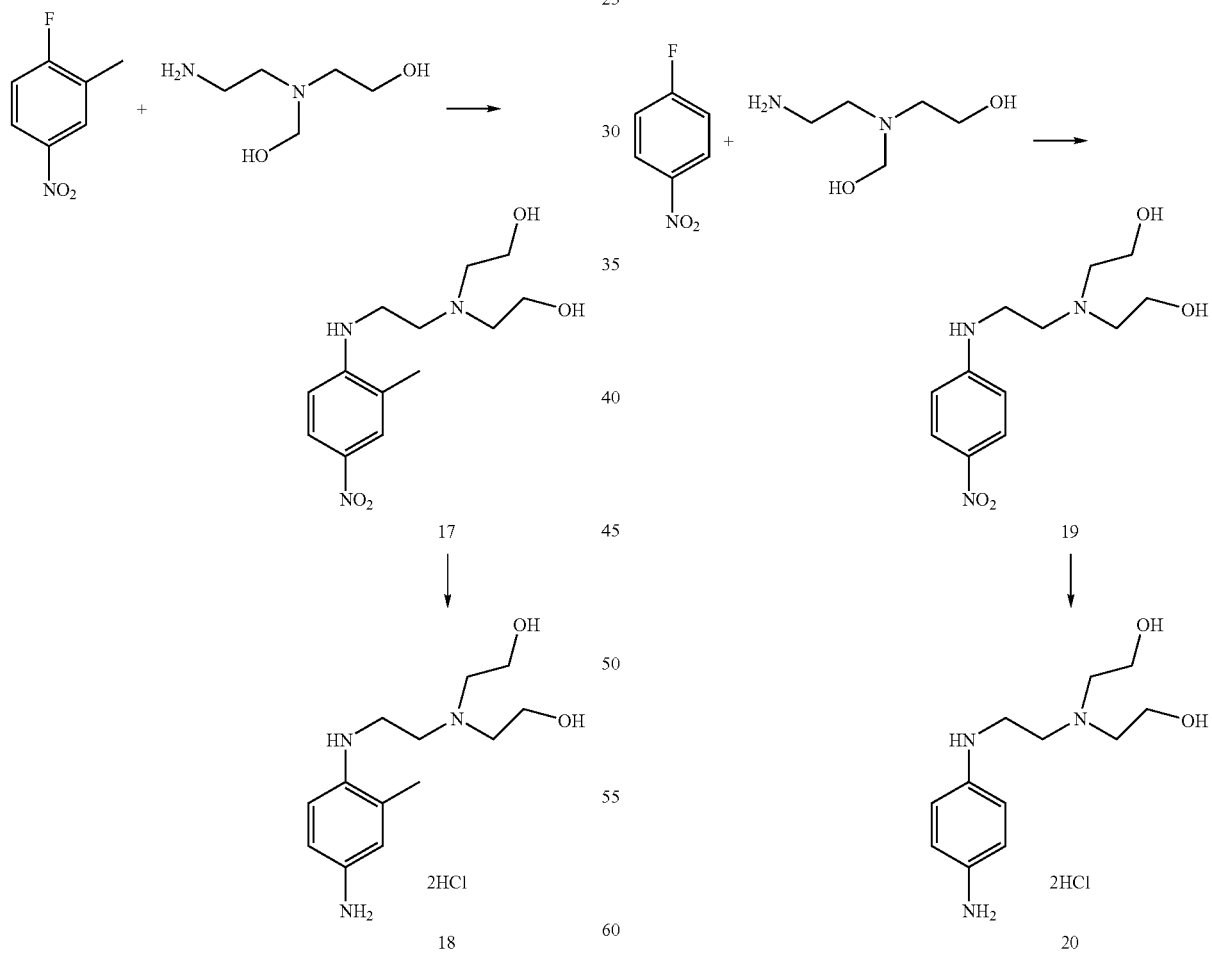

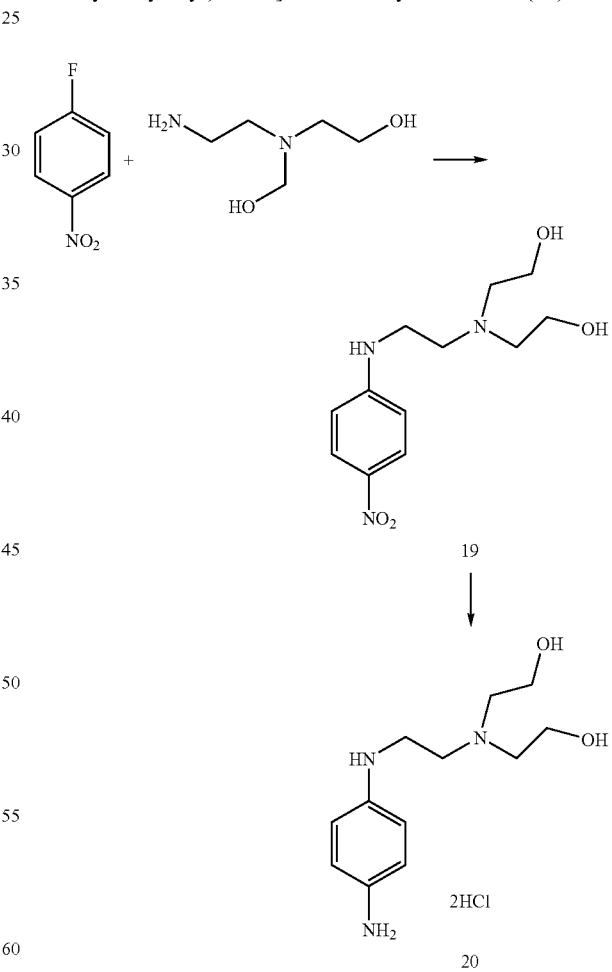

Step 1: Synthesis of 2-[[2-(4-nitro-2-methylphenylamino)ethyl]-(2-hydroxyethyl)amino]ethanol (17)

2 g of 2-fluoro-5-nitrotoluene were added to a solution of 30 ml of N-methylpyrrolidinone, 2.29 g of N,N-bis(2-hydroxyethyl)ethylenediamine, and 1.72 g of triethylamine.

Step 1: Synthesis of 2-[[-(4-nitrophenylamino)ethyl]-(2-hydroxyethyl)amino]ethanol (19)

5 g of para-fluoronitrobenzene were added to a solution of 60 ml of N-methylpyrrolidinone, 6.29 g of N,N-bis(2-hydroxyethyl)ethylenediamine, and 4.3 g of triethylamine. The reaction medium was heated at 60° C. for 15 hours and, after cooling to room temperature, was poured into a water/ice mixture. A yellow precipitate formed, which was filtered off, reslurried in water, and then dried over $P_2O_5$. 7.5 g of 2-[[2-(4-nitrophenylamino)ethyl]-(2-hydroxyethyl)amino]ethanol (19) were obtained.

Step 2: Synthesis of 2-[[2-(4-aminophenylamino)ethyl]-(2-hydroxyethyl)amino]ethanol Dihydrochloride (20)

The 2-[[2-(4-nitrophenylamino)ethyl]-(2-hydroxyethyl)amino]ethanol (19) obtained above was reduced with a boiling zinc/ammonium chloride/water/ethanol mixture. The corresponding amine was isolated in dihydrochloride form.

The proton NMR and mass spectra were in accordance with the expected structure of the product.

Example 11

Synthesis of 2-(4-amino-2-methylphenylamino)octadecane-1,3-diol (22)

Step 1: Preparation of 2-[(2-methyl-4-nitrophenyl)amino]octadecane-1,3-diol (21)

51 mg (0.00033 mol) of 2-fluoro-5-nitrotoluene, 37 mg (0.00035 mol) of sodium carbonate, and 3 ml of NMP were introduced into a three-necked flask. 100 mg (0.00033 mol) of DL-1,3-dihydroxy-2-aminooctadecane (DL-dihydrosphingosine) in 3 ml of NMP were added dropwise with stirring. The mixture was heated to 90° C. After reaction for 6 days, the reaction mixture was cooled and 5 ml of distilled water were then added slowly with vigorous stirring. A dark yellow semi-solid precipitate appeared. This precipitate was filtered off, washed several times with water and then with pentane, and dried under vacuum. The crude product obtained was purified on a column of silica, eluting with 2/3 ethyl acetate/heptane. 35 mg of expected nitro derivative (21) were obtained in the form of a yellow solid.

Step 2: Preparation of 2-(4-amino-2-methylphenylamino)octadecane-1,3-diol (22)

The 2-[(2-methyl-4-nitrophenyl)amino]octadecane-1,3-diol (21) obtained above was reduced with a boiling zinc/ammonium chloride/water/ethanol mixture. The corresponding amine was isolated in dihydrochloride form.

The proton NMR and mass spectra were in accordance with the expected structure of the product.

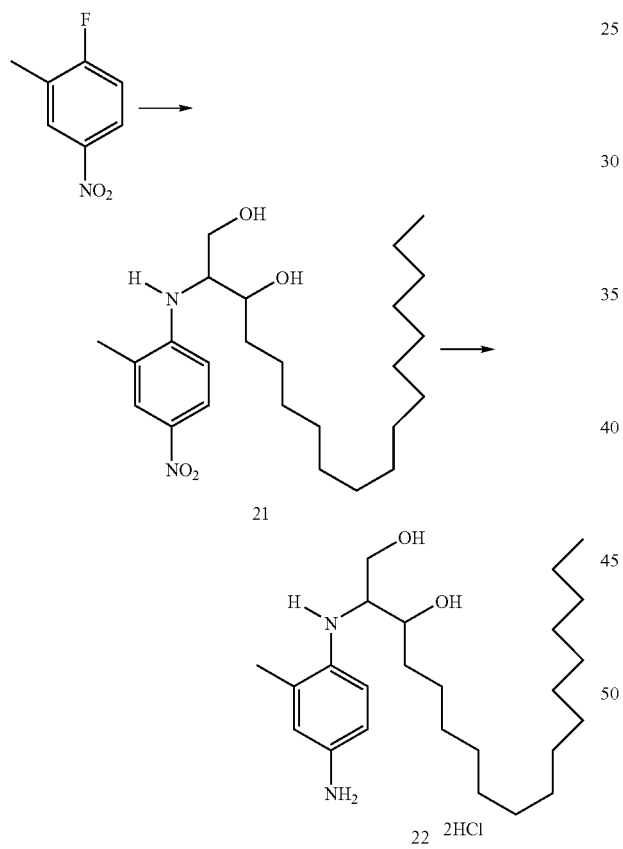

-B- Dyeing Examples

Examples 12 to 21

Dye composition from 2-(4-aminophenylamino)octadecane-1,3-diol Dihydrochloride (4)

Examples 12 to 17

Dyeing in Acidic Medium

The following dye compositions were prepared:

|  | Example | | | | | |
|---|---|---|---|---|---|---|
|  | 12 | 13 | 14 | 15 | 16 | 17 |
| 2-(4-Aminophenyl-amino)octadecane-1,3-diol dihydrochloride (4) | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | |

-continued

| | | | | | | |
|---|---|---|---|---|---|---|
| 5-Amino-2-methylphenol | $10^{-3}$ mol | | | | | |
| 1H-Indol-6-ol | | $10^{-3}$ mol | | | | |
| 2-Aminopyridin-3-ol | | | $10^{-3}$ mol | | | |
| 3,6-Dimethyl-1H-pyrazolo[5,1-c]-[1,2,4]triazole | | | | $10^{-3}$ mol | | |
| 2-(2,4-Diaminophenoxy)-ethanol hydrochloride | | | | | $10^{-3}$ mol | |
| Dye support (1) | (*) | (*) | (*) | (*) | (*) | (*) |
| Demineralized water qs | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

| | Example | | | | | |
|---|---|---|---|---|---|---|
| | 12 | 13 | 14 | 15 | 16 | 17 |
| Shade observed | strong grey | strong blue-violet grey | strong red-brown | strong grey | strong grey | strong blue-violet |

Examples 18 to 21

Dyeing in Basic Medium

The following dye compositions were prepared:

| | Example | | | |
|---|---|---|---|---|
| | 18 | 19 | 20 | 21 |
| 2-(4-Aminophenylamino)-octadecane-1,3-diol dihydrochloride (4) | $10^{-3}$ mol | $10^{-3}$ mol | $10^{-3}$ mol | $10^{-3}$ mol |
| 5-Amino-2-methylphenol | $10^{-3}$ mol | | | |
| 1H-Indol-6-ol | | $10^{-3}$ mol | | |
| 3,6-Dimethyl-1H-pyrazolo[5,1-c][1,2,4]-triazole | | | $10^{-3}$ mol | |
| 2-(2,4-Diaminophenoxy)-ethanol hydrochloride | | | | $10^{-3}$ mol |

| -continued | | | | |
|---|---|---|---|---|
| Dye support (2) | (*) | (*) | (*) | (*) |
| Demineralized water qs | 100 g | 100 g | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

| | Example | | | |
|---|---|---|---|---|
| | 18 | 19 | 20 | 21 |
| Shade observed | red | orange | chromatic red | strong blue |

Examples 22 to 28

Dye composition from 2-(4-phenylamino)methylpropane-1,3-diol Dihydrochloride (2)

Examples 22 to 25

Dyeinq in Acidic Medium

The following dye compositions were prepared:

| | Example | | | |
|---|---|---|---|---|
| | 22 | 23 | 24 | 25 |
| 2-Methylpropane-1,3-diol dihydrochloride (2) | $10^{-3}$ mol | $10^{-3}$ mol | $10^{-3}$ mol | $10^{-3}$ mol |
| 1H-Indol-6-ol | $10^{-3}$ mol | | | |
| 2-Aminopyridin-3-ol | | $10^{-3}$ mol | | |
| 2-(2,4-Diaminophenoxy)-ethanol hydrochloride | | | $10^{-3}$ mol | |
| 3-Amino-2-chloro-6-methylphenol hydrochloride | | | | $10^{-3}$ mol |
| Dye support (1) | (*) | (*) | (*) | (*) |
| Demineralized water qs | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again and then dried. The shades obtained are given in the table below:

|  | Example | | | |
|---|---|---|---|---|
|  | 22 | 23 | 24 | 25 |
| Shade observed | orange-brown | red brown | blue grey | violet grey |

Examples 26 to 28

Dyeing in Basic Medium

The following dye compositions were prepared:

|  | Example | | |
|---|---|---|---|
|  | 26 | 27 | 28 |
| 2-Methylpropane-1,3-diol dihydrochloride (2) | $10^{-3}$ mol | $10^{-3}$ mol | $10^{-3}$ mol |
| 5-Amino-2-methylphenol | $10^{-3}$ mol | | |
| 2-(2,4-Diaminophenoxy)-ethanol hydrochloride | | $10^{-3}$ mol | |
| 3-Amino-2-chloro-6-methylphenol hydrochloride | | | $10^{-3}$ mol |
| Dye support (2) | (*) | (*) | (*) |
| Demineralized water qs | 100 g | 100 g | 100 g |

(*): dye support (2) pH 9.5

| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

|  | Example | | |
|---|---|---|---|
|  | 26 | 27 | 28 |
| Shade observed | red | blue | violet |

Examples 29 to 34

Dye Composition from 2-(4-Aminophenylamino)-2-hydroxymethylpropane-1,3-diol (6)

Examples 29 to 32

Dyeing in Acidic Medium

The following dye compositions were prepared:

|  | Example | | | |
|---|---|---|---|---|
|  | 29 | 30 | 31 | 32 |
| 2-(4-Aminophenylamino)-2-hydroxymethylpropane-1,3-diol (6) | $10^{-3}$ mol | $10^{-3}$ mol | $10^{-3}$ mol | $10^{-3}$ mol |
| 1H-Indol-6-ol | $10^{-3}$ mol | | | |
| 2-Aminopyridin-3-ol | | $10^{-3}$ mol | | |
| 2-(2,4-Diaminophenoxy)-ethanol hydrochloride | | | $10^{-3}$ mol | |
| 3-Amino-2-chloro-6-methylphenol hydrochloride | | | | $10^{-3}$ mol |

-continued

| Dye support (1) Demineralized water qs | (*) 100 g | (*) 100 g | (*) 100 g | (*) 100 g |
|---|---|---|---|---|

(*): Dye support (1) pH 7

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

| | Example | | | |
|---|---|---|---|---|
| | 29 | 30 | 31 | 32 |
| Shade observed | orange-brown | red brown | blue | violet |

Examples 33 to 34

Dyeing in Basic Medium

The dye compositions below were prepared:

| | Example | |
|---|---|---|
| | 33 | 34 |
| 2-(4-Amino-phenylamino)-2-hydroxymethylpropane-1,3-diol (6) | $10^{-3}$ mol | $10^{-3}$ mol |
| 2-(2,4-Diaminophenoxy) ethanol hydrochloride | $10^{-3}$ mol | |
| 3-Amino-2-chloro-6-methylphenol hydrochloride | | $10^{-3}$ mol |

-continued

| Dye support (2) | (*) | (*) |
|---|---|---|
| Demineralized water qs | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, the composition was mixed with an equal weight of 20-volumes aqueous hydrogen peroxide solution (6% by weight). A final pH of 9.5 was obtained.

The mixture obtained was applied to locks of grey hair containing 90% white hairs. 30 minutes after application, the locks were rinsed, washed with a standard shampoo, rinsed again and then dried.

The shades obtained are given in the table below:

| | Example | |
|---|---|---|
| | 33 | 34 |
| Shade observed | blue | violet |

Examples 35 to 43
Dye Composition using 2-(4-aminophenylamino)propane-1.3-diol Dihydrochloride (16)
Examples 35 to 40
Dyeing in Acidic Medium The following dye compositions were prepared:

|  | Example | | | | | |
| --- | --- | --- | --- | --- | --- | --- |
|  | 35 | 36 | 37 | 38 | 39 | 40 |
| 2-(4-Aminophenyl-amino)propane-1,3-diol dichlorhydrate (16) | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | |
| 5-Amino-2-methylphenol | | $10^{-3}$ mol | | | | |
| 1H-Indol-6-ol | | | $10^{-3}$ mol | | | |
| 3,6-Dimethyl-1H-pyrazolo[5,1-c][1,2,4]triazole | | | | $10^{-3}$ mol | | |
| 2-(2,4-Diamino-phenoxy)ethanol hydrochloride | | | | | $10^{-3}$ mol | |
| 3-Amino-2-chloro-6-methyl-phenol hydrochloride | | | | | | $10^{-3}$ mol |
| Dye support (1) | (*) | (*) | (*) | (*) | (*) | (*) |
| Demineralized water qs | 100 g | 100 g | 100 g | 100 g | 100 g | 100 g |

| (*): Dye support (1) pH 7 | |
| --- | --- |
| 96° Ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| C8-C10 Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

|  | Example | | | | | |
| --- | --- | --- | --- | --- | --- | --- |
|  | 35 | 36 | 37 | 38 | 39 | 40 |
| Shade observed | yellow-brown | strong red-violet | brown | red-brown | strong blue-grey | strong blue-violet |

Examples 41 to 43
Dyeing in Basic Medium

The following dye compositions were prepared:

|  | Example | | |
| --- | --- | --- | --- |
|  | 41 | 42 | 43 |
| 2-(4-Aminophenylamino)propane-1,3-diol dichlorhydrate (16) | $10^{-3}$ mol | $10^{-3}$ mol | $10^{-3}$ mol |
| 5-Amino-2-methylphenol | $10^{-3}$ mol | | |
| 2-(2,4-Diaminophenoxy)ethanol hydrochloride | | $10^{-3}$ mol | |
| 3-Amino-2-chloro-6-methylphenol hydrochloride | | | $10^{-3}$ mol |
| Dye support (2) | (*) | (*) | (*) |
| Demineralized water qs | 100 g | 100 g | 100 g |

| (*): Dye support (2) pH 9.5 | |
| --- | --- |
| 96° Ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

|  | Example | | |
| --- | --- | --- | --- |
|  | 41 | 42 | 43 |
| Shade observed | red-violet grey | blue | strong blue-violet |

Examples 44 to 53

Dye Composition Using 3-(4-amino-2-methylphenylamino)propane-1,2-diol dihydrochloride (8)

Examples 44 to 49

Dyeing in Acidic Medium

The following dye compositions were prepared:

|  | Example | | | | | |
| --- | --- | --- | --- | --- | --- | --- |
|  | 44 | 45 | 46 | 47 | 48 | 49 |
| 3-(4-Amino-2-methyl-phenylamino)propane-1,2-diol dihydrochloride (8) | $10^{-3}$ mol | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | | |
| 1H-Indol-6-ol | | $10^{-3}$ mol | | | | |
| 2-Amino-pyridin-3-ol | | | $10^{-3}$ mol | | | |
| 3,6-Dimethyl-1H-pyrazolo[5,1-c][1,2,4]-triazole | | | | $10^{-3}$ mol | | |
| 2-(2,4-Diaminophenoxy)-ethanol hydrochloride | | | | | $10^{-3}$ mol | |
| 3-Amino-2-chloro-6-methylphenol hydrochloride | | | | | | $10^{-3}$ mol |
| Dye support (1) | (*) | (*) | (*) | (*) | (*) | (*) |
| Demineralized water qs | 100 g | 100 g | 100 g | 100 g | 100 g | 100 g |

(*): Dye support (1) pH 7

| | |
| --- | --- |
| 96° Ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

|  | Example | | | | | |
|---|---|---|---|---|---|---|
|  | 44 | 45 | 46 | 47 | 48 | 49 |
| Shade observed | strong violet | brown | strong red-brown | orange | strong blue | strong blue-violet |

Examples 50 to 53

Dyeing in Basic Medium

The following dye compositions were prepared:

|  | Example | | | |
|---|---|---|---|---|
|  | 50 | 51 | 52 | 53 |
| 3-(4-Amino-2-methylphenylamino)-propane-1,2-diol dihydrochloride (8) | $10^{-3}$ mol | $10^{-3}$ mol | $10^{-3}$ mol | $10^{-3}$ mol |
| 5-Amino-2-methylphenol | $10^{-3}$ mol | | | |
| 3,6-Dimethyl-1H-pyrazolo[5,1-c][1,2,4]triazole | | $10^{-3}$ mol | | |
| 2-(2,4-Diaminophenoxy)ethanol hydrochloride | | | $10^{-3}$ mol | |
| 3-Amino-2-chloro-6-methylphenol hydrochloride | | | | $10^{-3}$ mol |
| Dye support (2) | (*) | (*) | (*) | (*) |
| Demineralized water qs | 100 g | 100 g | 100 g | 100 g |

| (*): Dye support (2) pH 9.5 | |
|---|---|
| 96° Ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

|  | Example | | | |
|---|---|---|---|---|
|  | 50 | 51 | 52 | 53 |
| Shade observed | red-violet | chromatic red | strong blue | strong blue-violet |

Examples 54 to 62

Dye Composition Using 3-(4-amino-3-methylphenylamino)propane-1,2-diol Dihydrochloride (10)

Examples 54 to 58

Dyeing in Acidic Medium

The following dye compositions were prepared:

|  | Example | | | | |
|---|---|---|---|---|---|
|  | 54 | 55 | 56 | 57 | 58 |
| 3-(4-Amino-3-methylphenyl-amino)propane-1,2-diol dihydrochloride (10) | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | |
| 1H-Indol-6-ol | | $10^{-3}$ mol | | | |
| 2-Aminopyridin-3-ol | | | $10^{-3}$ mol | | |
| 2-(2,4-Diaminophenoxy)-ethanol hydrochloride | | | | $10^{-3}$ mol | |
| 3-Amino-2-chloro-6-methylphenol hydrochloride | | | | | $10^{-3}$ mol |
| Dye support (1) | (*) | (*) | (*) | (*) | (*) |
| Demineralized water qs | 100 g | 100 g | 100 g | 100 g | 100 g |

| (*): Dye support (1) pH 7 | |
|---|---|
| 96° Ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

|  | Example | | | | |
|---|---|---|---|---|---|
|  | 54 | 55 | 56 | 57 | 58 |
| Shade observed | strong violet-grey | orange-brown | yellow-brown | strong blue-green grey | strong blue |

Examples 59 to 62

Dyeing in Basic Medium

The following dye compositions were prepared:

|  | Example | | | |
|---|---|---|---|---|
|  | 59 | 60 | 61 | 62 |
| 3-(4-Amino-3-methylphenylamino)propane-1,2-diol dihydrochloride (10) | $10^{-3}$ mol | $10^{-3}$ mol | $10^{-3}$ mol | $10^{-3}$ mol |
| 5-Amino-2-methylphenol | $10^{-3}$ mol | | | |
| 3,6-Dimethyl-1H-pyrazolo[5,1-c][1,2,4]-triazole | | $10^{-3}$ mol | | |

-continued

| | | | | |
|---|---|---|---|---|
| 2-(2,4-Diamino-phenoxy)ethanol hydrochloride | | | $10^{-3}$ mol | |
| 3-Amino-2-chloro-6-methylphenol hydrochloride | | | | $10^{-3}$ mol |
| Dye support (2) | (*) | (*) | (*) | (*) |
| Demineralized water qs | 100 g | 100 g | 100 g | 100 g |

| | |
|---|---|
| (*): Dye support (2) pH 9.5 | |
| 96° Ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

| | Example | | | |
|---|---|---|---|---|
| | 59 | 60 | 61 | 62 |
| Shade observed | violet | chromatic red | blue-green | strong blue |

Examples 63 to 71

Dye Composition Using 2-(4-amino-3-methylphenylamino)propane-1.3-diol Dihydrochloride (12)

| | Example | | | | |
|---|---|---|---|---|---|
| | 63 | 64 | 65 | 66 | 67 |
| 2-(4-Amino-3-methylphenyl-amino)propane-1,3-diol dihydrochloride (12) | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | |
| 1H-Indol-6-ol | | $10^{-3}$ mol | | | |
| 2-Aminopyridin-3-ol | | | $10^{-3}$ mol | | |
| 2-(2,4-Diaminophenoxy)-ethanol hydrochloride | | | | $10^{-3}$ mol | |
| 3-Amino-2-chloro-6-methylphenol hydrochloride | | | | | $10^{-3}$ mol |
| Dye support (1) | (*) | (*) | (*) | (*) | (*) |
| Demineralized water qs | 100 g | 100 g | 100 g | 100 g | 100 g |

| | |
|---|---|
| (*): Dye support (1) pH 7 | |
| 96° Ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

|  | Example | | | | |
| --- | --- | --- | --- | --- | --- |
|  | 63 | 64 | 65 | 66 | 67 |
| Shade observed | strong violet-grey | red-brown | orange-brown | strong blue-green grey | strong blue |

Examples 68 to 71

Dyeing in Basic Medium

The following dye compositions were prepared:

|  | Example | | | |
| --- | --- | --- | --- | --- |
|  | 68 | 69 | 70 | 71 |
| 2-(4-Amino-3-methylphenylamino) propane-1,3-diol dihydrochloride (12) | $10^{-3}$ mol | $10^{-3}$ mol | $10^{-3}$ mol | $10^{-3}$ mol |
| 5-Amino-2-methylphenol | $10^{-3}$ mol | | | |
| 3,6-Dimethyl-1H-pyrazolo[5,1-c][1,2,4]triazole | | $10^{-3}$ mol | | |
| 2-(2,4-Diaminophenoxy)ethanol hydrochloride | | | $10^{-3}$ mol | |
| 3-Amino-2-chloro-6-methylphenol hydrochloride | | | | $10^{-3}$ mol |
| Dye support (2) | (*) | (*) | (*) | (*) |
| Demineralized water qs | 100 g | 100 g | 100 g | 100 g |

(*): Dye support (2) pH 9.5

| | |
| --- | --- |
| 96° Ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

|  | Example | | | |
|---|---|---|---|---|
|  | 68 | 69 | 70 | 71 |
| Shade observed | violet-grey | chromatic red | blue-green | strong blue |

Examples 72 to 85

Dye Composition Using 2-[[2-(4-aminophenylamino)ethyl]-(2-hydroxyethyl)amino]ethanol Dihydrochloride (20)

Examples 72 to 78

Dyeing in Acidic Medium

The following dye compositions were prepared:

|  | Example | | | | | | |
|---|---|---|---|---|---|---|---|
|  | 72 | 73 | 74 | 75 | 76 | 77 | 78 |
| 2-[[2-(4-Aminophenyl-amino)ethyl]-(2-hydroxyethyl)amino]ethanol dihydrochloride (20) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c][1,2,4]triazole | | | | | $10^{-3}$ mol | | |
| 2-(2,4-Diaminophenoxy)-ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): Dye support (1) pH 7

| | |
|---|---|
| 96° Ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

|  | Example | | | | | | |
|---|---|---|---|---|---|---|---|
|  | 72 | 73 | 74 | 75 | 76 | 77 | 78 |
| Shade observed | strong orange-brown | strong red | strong brown | strong red | orange | strong blue-grey | strong red-violet |

Examples 79 to 85

Dyeinq in Basic Medium

The following dye compositions were prepared:

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

|  | Example | | | | | | |
|---|---|---|---|---|---|---|---|
|  | 79 | 80 | 81 | 82 | 83 | 84 | 85 |
| Shade observed | orange | red | orange | red | chromatic red | strong blue-violet | strong violet |

|  | Example | | | | | | |
|---|---|---|---|---|---|---|---|
|  | 79 | 80 | 81 | 82 | 83 | 84 | 85 |
| 2-[[2-(4-Aminophenyl-amino)ethyl]-(2-hydroxyethyl)amino]-ethanol dihydrochloride (20) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c][1,2,4]-triazole | | | | | $10^{-3}$ mol | | |
| 2-(2,4-Diamino-phenoxy)ethanol hydrochloride | | | | | | $10^{-3}$ mol | |
| 3-Amino-2-chloro-6-methylphenol hydrochloride | | | | | | | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*): Dye support (2) pH 9.5

| | |
|---|---|
| 96° Ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

Examples 86 to 92

Dye Composition Using 2-(4-amino-2-methylphenylamino)propane-1,3-diol Dihydrochloride (14)

Examples 86 to 90

Dyeing in Acidic Medium

The following dye compositions were prepared:

|  | Example | | | | |
| --- | --- | --- | --- | --- | --- |
|  | 86 | 87 | 88 | 89 | 90 |
| 2-(4-Amino-2-methylphenyl-amino)propane-1,3-diol dihydrochloride (14) | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | |
| 1H-Indol-6-ol | | $10^{-3}$ mol | | | |
| 2-Aminopyridin-3-ol | | | $10^{-3}$ mol | | |
| 2-(2,4-Diaminophenoxy)-ethanol hydrochloride | | | | $10^{-3}$ mol | |
| 3-Amino-2-chloro-6-methylphenol hydrochloride | | | | | $10^{-3}$ mol |
| Dye support (1) | (*) | (*) | (*) | (*) | (*) |
| Demineralized water qs | 100 g | 100 g | 100 g | 100 g | 100 g |

(*): Dye support (1) pH 7

| | |
| --- | --- |
| 96° Ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

|  | Example | | | | |
|---|---|---|---|---|---|
|  | 86 | 87 | 88 | 89 | 90 |
| Shade observed | strong violet | brown | brown | strong blue | strong blue-violet |

Examples 91 to 92

Dyeing in Basic Medium

The following dye compositions were prepared:

|  | Example | |
|---|---|---|
|  | 91 | 92 |
| 2-(4-Amino-2-methylphenylamino)-propane-1,3-diol dihydrochloride (14) | $10^{-3}$ mol | $10^{-3}$ mol |
| 2-(2,4-Diaminophenoxy)ethanol hydrochloride | $10^{-3}$ mol |  |
| 3-Amino-2-chloro-6-methylphenol hydrochloride |  | $10^{-3}$ mol |

-continued

|  | Example | |
|---|---|---|
|  | 91 | 92 |
| Dye support (2) | (*) | (*) |
| Demineralized water qs | 100 g | 100 g |

(*): Dye support (2) pH 9.5
| | |
|---|---|
| 96° Ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| C8-C10 Alkyl polyglucoside as an aqueous 60% solution | 3.6 g A.M. |
| Benzyl alcohol | 2.0 g |
| Polyethylene glycol containing 8 ethylene oxide units | 3.0 g |
| NH$_4$Cl | 4.32 g |
| Aqueous ammonia containing 20% NH$_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

|  | Example | |
|---|---|---|
|  | 91 | 92 |
| Shade observed | blue | strong blue-violet |

Examples 93 to 103

Dye Composition Using 2-[[2-(4-amino-2-methylphenylamino)ethyl]-(2-hydroxyethyl)amino]ethanol Dihydrochloride (18)

Examples 93 to 99

Dyeing in Acidic Medium

The following dye compositions were prepared:

|  | Example | | | | | | |
|---|---|---|---|---|---|---|---|
|  | 93 | 94 | 95 | 96 | 97 | 98 | 99 |
| 2-[[2-(4-Amino-2-methylphenylamino)ethyl]-(2-hydroxyethyl)amino]ethanol dihydrochloride (18) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol |  |  |  |  |  |  |
| 5-Amino-2-methylphenol |  | $10^{-3}$ mol |  |  |  |  |  |
| 1H-Indol-6-ol |  |  | $10^{-3}$ mol |  |  |  |  |
| 2-Aminopyridin-3-ol |  |  |  | $10^{-3}$ mol |  |  |  |
| 3,6-Dimethyl-1H-pyrazolo-[5,1-c][1,2,4]triazole |  |  |  |  | $10^{-3}$ mol |  |  |
| 2-(2,4-Diaminophenoxy)-ethanol hydrochloride |  |  |  |  |  | $10^{-3}$ mol |  |
| 3-Amino-2-chloro-6-methyl-phenol hydrochloride |  |  |  |  |  |  | $10^{-3}$ mol |

| | | | | | | | |
|---|---|---|---|---|---|---|---|
| Dye support (1) | (*) | (*) | (*) | (*) | (*) | (*) | (*) |
| Demineralized water qs | 100 g | 100 g | 100 g | 100 g | 100 g | 100 g | 100 g |

| (*): Dye support (1) pH 7 | |
|---|---|
| 96° Ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

| | Example | | | | | | |
|---|---|---|---|---|---|---|---|
| | 93 | 94 | 95 | 96 | 97 | 98 | 99 |
| Shade observed | orange | strong red | orange-brown | strong red | orange | strong blue-grey | strong violet |

Examples 100 to 103

Dyeing in Basic Medium

The following dye compositions were prepared:

| | Example | | | |
|---|---|---|---|---|
| | 100 | 101 | 102 | 103 |
| 2-[[2-(4-Amino-2-methylphenylamino)ethyl]-(2-hydroxyethyl)amino]ethanol dihydrochloride (18) | $10^{-3}$ mol | $10^{-3}$ mol | $10^{-3}$ mol | $10^{-3}$ mol |
| 5-Amino-2-methylphenol | $10^{-3}$ mol | | | |
| 3,6-Dimethyl-1H-pyrazolo[5,1-c][1,2,4]triazole | | $10^{-3}$ mol | | |
| 2-(2,4-Diaminophenoxy)ethanol hydrochloride | | | $10^{-3}$ mol | |
| 3-Amino-2-chloro-6-methylphenol hydrochloride | | | | $10^{-3}$ mol |
| Dye support (2) | (*) | (*) | (*) | (*) |
| Demineralized water qs | 100 g | 100 g | 100 g | 100 g |

| (*): Dye support (2) pH 9.5 | |
|---|---|
| 96° Ethyl alcohol | 20.8 g |
| Sodium metabisulfite as an aqueous 35% solution | 0.23 g A.M. |
| Pentasodium salt of diethylenetriaminepentaacetic acid as an aqueous 40% solution | 0.48 g A.M. |
| $C_8$-$C_{10}$ Alkyl polyglucoside as an aqueous 60% solution | 3.6 g A.M. |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. 30 minutes after application, the locks were rinsed, washed with a standard shampoo, rinsed again and then dried.

The shades obtained are given in the table below:

| | Example | | | |
|---|---|---|---|---|
| | 100 | 101 | 102 | 103 |
| Shade observed | red | chromatic red | strong blue | strong violet |

What is claimed is:

1. A secondary para-phenylene diamine chosen from compounds of formula (I) and the addition salts thereof:

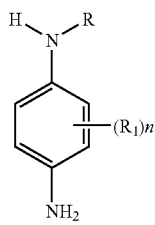

wherein:
R is chosen from linear and branched $C_2$-$C_{18}$ alkyl radicals comprising from 2 to 4 hydroxyl groups, wherein the alkyl radicals are unsubstituted or substituted with at least one entity chosen from amino, mono($C_1$-$C_{15}$)alkylamino, di($C_1$-$C_{15}$)alkylamino, ($C_1$-$C_{15}$)alkylcarbonyl, amido, mono($C_1$-$C_{15}$)alkylaminocarbonyl, and di($C_1$-$C_{15}$)alkylaminocarbonyl groups, and wherein the alkyl radicals are interrupted with at least one heteroatom chosen from oxygen and nitrogen;

$R_1$ is chosen from hydrogen, $C_1$-$C_5$ alkyl radicals, $C_1$-$C_{15}$ alkoxy radicals, hydroxy(($C_1$-$C_{15}$)alkoxy) radicals, ($C_1$-$C_{15}$)alkoxy($C_1$-$C_{15}$)alkyl radicals, $C_1$-$C_{15}$ monohydroxyalkyl radicals, $C_1$-$C_{15}$ polyhydroxyalkyl radicals, and halogen atoms; and n is an integer ranging from 1 to 4;
with the proviso that the compound of formula (I) is not N-(2,3-dihydroxypropyl)-para-phenylenediamine.

2. The secondary para-phenylene diamine according to claim 1, wherein $R_1$ is chosen from hydrogen, and $C_1$-$C_6$ alkyl and $C_1$-$C_6$ alkoxy radicals.

3. The secondary para-phenylene diamine according to claim 1, wherein the compound of formula (I) is chosen from:
2-[[2-(4-Aminophenylamino)ethyl]-(2-hydroxyethyl)amino]ethanol;
2-[[2-(4-Amino-2-methylphenylamino)ethyl]-(2-hydroxyethyl)amino]ethanol;
2-[[2-(4-Amino-3-methylphenylamino)ethyl]-(2-hydroxyethyl)amino]ethanol;
3-[3-[4-Aminophenylamino)propoxylpropane-1,2-diol; and
2-[[4-(4-Aminophenylamino)butyl]-(2-hydroxyethyl)amino]ethanol.

4. The secondary para-phenylene diamine according to claim 1, wherein the addition salts of the compounds of formula (I) are acid addition salts chosen from hydrochlorides, hydrobromides, sulfates, citrates, succinates, tartrates, lactates, tosylates, benzenesulfonates, phosphates, and acetates.

5. A cosmetic composition for dyeing keratin fibers,: comprising, in a medium that is suitable for dyeing, at least one compound chosen from those of formula (I) and the addition salts thereof:

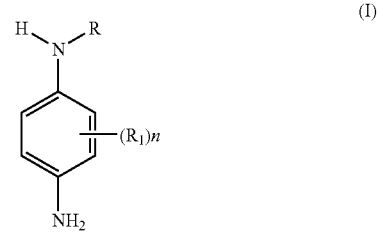

wherein:
R is chosen from linear and branched $C_2$-$C_{18}$ alkyl radicals comprising from 2 to 4 hydroxyl groups, wherein the alkyl radicals are unsubstituted or substituted with at least one entity chosen from amino, mono($C_1$-$C_{15}$)alkylamino, di($C_1$-$C_{15}$)alkylamino, ($C_1$-$C_{15}$)alkylcarbonyl, amido, mono($C_1$-$C_{15}$)alkylaminocarbonyl, and di($C_1$-$C_{15}$)alkylaminocarbonyl groups, and wherein the alkyl radicals are interrupted with at least one heteroatom chosen from oxygen and nitrogen;

$R_1$, is chosen from hydrogen, $C_1$-$C_{15}$ alkyl radicals, $C_1$-$C_{15}$ alkoxy radicals, hydroxy(($C_1$-$C_{15}$)alkoxy) radicals, ($C_1$-$C_{15}$)alkoxy($C_1$-$C_{15}$)alkyl radicals, $C_1$-$C_{15}$ monohydroxyalkyl radicals, $C_1$-$C_{15}$ polyhydroxyalkyl radicals, and halogen atoms; and n is an integer ranging from 1 to 4;
with the proviso that the compound of formula (I) is not N-(2,3-dihydroxypropyl)-para-phenylenediamine.

6. The cosmetic composition according to claim 5, wherein $R_1$ is chosen from hydrogen, and $C_1$-$C_6$ alkyl and $C_1$-$C_6$ alkoxy radicals.

7. The cosmetic composition according to claim 5, wherein the compound of formula (I) is chosen from:
[[2-(4-Aminophenylamino)ethyl]-(2-hydroxyethyl)amino]ethanol;
2-[[2-(4-Amino-2-methylphenylamino)ethyl]-(2-hydroxyethyl)amino]ethanol;
2-[[2-(4-Amino-3-methylphenylamino)ethyl]-(2-hydroxyethyl)amino]ethanol
3-[3-[4-Aminophenylamino)propoxylpropane-1,2-diol; and
2-[[4-(4-Aminophenylamino)butyl]-(2-hydroxyethyl)amino]ethanol.

8. The composition according to claim 5, wherein the addition salts of the compounds of formula (I) are acid addition salts chosen from hydrochlorides, hydrobromides, sulfates, citrates, succinates, tartrates, lactates, tosylates, benzenesulfonates, phosphates and acetates.

9. The composition according to claim 5, wherein the at least one: compound of formula (I) is present in an amount ranging from 0.0001% to 20% by weight, relative to the total weight of the composition.

10. The composition according to claim 5, wherein the medium that is suitable for dyeing comprises water or comprises a mixture of water and of at least one organic solvent chosen from branched and unbranched $C_1$-$C_4$ lower alcohols; polyols and polyol ethers; and aromatic alcohols.

11. The composition according to claim 5, further comprising at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents, opacifiers, vitamins and provitamins.

12. The composition according to claim 11, wherein the at least one cosmetic adjuvant is present, in an amount for each of them, ranging from 0.01% to 20% by weight, relative to the total weight of the composition.

13. The composition according to claim 5, further comprising at least one oxidation coupler chosen from meta-phenylenediamines, meta-aminophenols meta-diphenols, naphthalenetased couplers, heterocyclic couplers, and the addition salts thereof.

14. The composition according to claim 13, wherein the at least one oxidation coupler is present in an amount ranging from 0.0001% to 20% by weight, relative to the total weight of the composition.

15. The composition according to claim 5, further comprising at least one additional oxidation base other than those of formula (I), chosen from para-phenylenediamines, bis(phenyl)alkylenediamines, para-aminophenols, ortho-aminophenols, heterocyclic bases, and the addition salts thereof.

16. The composition according to claim 15, wherein the at least one additional oxidation base is present in an amount ranging from 0.0001% to 20% by weight, relative to the total weight of the composition.

17. The composition according to claim 5, further comprising at least one direct dye chosen from natural and cationic direct dyes.

18. A ready-to-use cosmetic composition, comprising, in a medium that is suitable for dyeing, at least one compound chosen from those of formula (I) and the addition salts thereof:

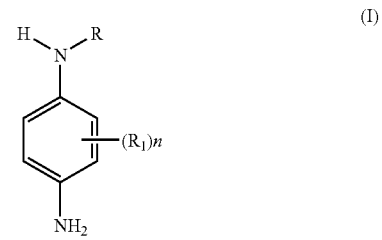

(I)

wherein:

R is chosen from linear and branched $C_2$-$C_{18}$ alkyl radicals comprising from 2 to 4 hydroxyl groups, wherein the alkyl radicals are unsubstituted or substituted with at least one entity chosen from amino, mono($C_1$-$C_{15}$)alkylamino, di($C_1$-$C_{15}$)alkylamino, ($C_1$-$C_{15}$)alkylcarbonyl, amido, mono($C_1$-$C_{15}$)alkylaminocarbonyl, and di($C_1$-$C_{15}$)alkylaminocarbonyl groups, and wherein the alkyl radicals are interrupted with at least one heteroatom chosen from oxygen and nitrogen;

$R_1$ is chosen from hydrogen, $C_1$-$C_{15}$ alkyl radicals, $C_1$-$C_{15}$ alkoxy radicals, hydroxy(($C_1$-$C_{15}$)alkoxy) radicals, ($C_1$-$C_{15}$)alkoxy($C_1$-$C_{15}$)alkyl radicals, $C_1$-$C_{15}$ monohydroxyalkyl radicals, $C_1$-$C_{15}$ polyhydroxyalkyl radicals, and halogen atoms; and n is an integer ranging from 1 to 4;

with the proviso that the compound of formula (I) is not N-(2,3-dihydroxypropyl)-para-phenylenediamine, and at least one oxidizing agent chosen from hydrogen peroxide, urea peroxide, alkali metal bromates, persalts, peracids, and oxidase enzymes.

* * * * *

UNITED STATES PATENT AND TRADEMARK OFFICE
CERTIFICATE OF CORRECTION

PATENT NO. : 7,591,860 B2
APPLICATION NO. : 11/066462
DATED : September 22, 2009
INVENTOR(S) : Stéphane Sabelle et al.

Page 1 of 1

It is certified that error appears in the above-identified patent and that said Letters Patent is hereby corrected as shown below:

In claim 1, column 61, line 43, "$C_1$-$C_5$" should read --$C_1$-$C_{15}$--.

In claim 5, column 62, line 5, "fibers,:" should read --fibers,--.

In claim 5, column 62, line 31, "$R_1$, is" should read --$R_1$ is--.

In claim 7, column 62, lines 49-50, "2-[[2-(4-Amino-3-methylphenylamino)ethyl]-(2-hydroxyethyl)amino]ethanol" should read
--2-[[2-(4-Amino-3-methylphenylamino)ethyl]-(2-hydroxyethyl)amino]ethanol;--.

In claim 9, column 62, line 62, "one: compound" should read --one compound--.

In claim 13, column 63, lines 15-16, "naphthalenetased" should read
--naphthalene-based--.

Signed and Sealed this

Twenty-fourth Day of November, 2009

David J. Kappos
*Director of the United States Patent and Trademark Office*